(12) United States Patent
Morita et al.

(10) Patent No.: US 12,044,654 B2
(45) Date of Patent: Jul. 23, 2024

(54) MEASUREMENT METHOD FOR NON-DESTRUCTIVE INSPECTION, MEASUREMENT DEVICE, NON-DESTRUCTIVE INSPECTION METHOD, INFORMATION PROCESSING DEVICE OF NON-DESTRUCTIVE INSPECTION, AND RECORDING MEDIUM

(71) Applicant: Konica Minolta, Inc., Tokyo (JP)

(72) Inventors: Hiroshi Morita, Narashino (JP); Katsunori Teshima, Kokubunji (JP); Mitsuru Mimori, Hino (JP); Yoshiyuki Hashimoto, Hachioji (JP); Motonori Takakura, Sagamihara (JP)

(73) Assignee: KONICA MINOLTA, INC., Tokyo (JP)

( * ) Notice: Subject to any disclaimer, the term of this patent is extended or adjusted under 35 U.S.C. 154(b) by 59 days.

(21) Appl. No.: 17/896,168

(22) Filed: Aug. 26, 2022

(65) Prior Publication Data
US 2023/0061607 A1  Mar. 2, 2023

(51) Int. Cl.
*G01N 27/82* (2006.01)
*G01N 33/2045* (2019.01)

(52) U.S. Cl.
CPC ......... *G01N 27/82* (2013.01); *G01N 33/2045* (2019.01)

(58) Field of Classification Search
CPC ............... G01N 27/82; G01N 33/2045
See application file for complete search history.

(56) References Cited

U.S. PATENT DOCUMENTS

| | | | | |
|---|---|---|---|---|
| 10,627,457 | B2* | 4/2020 | Sugiyama | G01R 33/063 |
| 2014/0252889 | A1* | 9/2014 | Beste | H02K 11/215 |
| | | | | 310/12.19 |
| 2018/0156637 | A1* | 6/2018 | Fesshaie | G01D 5/485 |
| 2022/0026397 | A1* | 1/2022 | Kamel | G01N 29/043 |

FOREIGN PATENT DOCUMENTS

WO     2020027028 A1    2/2020

* cited by examiner

*Primary Examiner* — Dominic E Hawkins
(74) *Attorney, Agent, or Firm* — CANTOR COLBURN LLP

(57) ABSTRACT

A measurement method is provided for non-destructive inspection of a magnetic material as an inspection target in a non-magnetic body. The method includes application of a magnetic field from a magnetic field applying unit to the inspection target through a surface of the non-magnetic body, and measurement of a magnetic field from the inspection target with a magnetic sensor on the surface of the non-magnetic body adjacent to the magnetic field applying unit at positions having different distances from the magnetic field applying unit in a first direction away from the magnetic field applying unit. The magnetic field from the inspection target is attenuated with the distances. In the method, first and second measurements are performed with the magnetic field applying unit respectively arranged on one side and on the other side in the first direction relative to the positions where the magnetic sensor performs measurement.

32 Claims, 14 Drawing Sheets

MEASUREMENT METHOD FOR NON-DESTRUCTIVE INSPECTION, MEASUREMENT DEVICE, NON-DESTRUCTIVE INSPECTION METHOD, INFORMATION PROCESSING DEVICE OF NON-DESTRUCTIVE INSPECTION, AND RECORDING MEDIUM

CROSS REFERENCE TO RELATED APPLICATIONS

The present invention claims priority under 35 U.S.C. § 119 to Japanese Application, 2021-139332, filed on Aug. 27, 2021, the entire contents of which being incorporated herein by reference.

BACKGROUND

Technological Field

The present invention relates to measurement and processing of measurement data in a magnetic non-destructive inspection.

Description of the Related Art

The range of applications of a magnetic non-destructive inspection includes a diagnosis of a corrosion- or deterioration-induced breakage in a magnetic material such as reinforcing steel, a steel rod, or a wire included in a non-magnetic material such as concrete or rubber, in particular, a diagnosis of a breakage in a PC steel material or reinforcing steel in a bridge pier, a bridge girder, or a floor slab of a road or a railroad.

A non-destructive inspection device described in WO 2020/027028 A1 has a configuration in which a magnetic field applying unit is arranged only on one side of a magnetic sensor, a magnetic field of a first polarity which is an N polarity or an S polarity is applied to an inspection target from the magnetic field applying unit such as a magnet, and the magnetic sensor senses a magnetic field from the inspection target in a state in which a magnetic field distribution that the magnetic field is attenuated within the range of the first polarity with distance from the magnetic field applying unit is formed. The magnetic field is measured with the magnetic sensor at a plurality of positions having different distances from the magnetic field applying unit in a first direction, and a magnetic field distribution in accordance with the distances from the magnetic field applying unit is obtained to determine an abnormality in the inspection target based on the magnetic field distribution.

The invention described in WO 2020/027028 A1 requires the magnetic field applying unit to be arranged only on the one side of the magnetic sensor, thus achieving reduction in size and weight of the device as well as favorable portability. As in the invention described in WO 2020/027028 A1, by applying a magnetic field to an inspection target, measuring a magnetic field from the inspection target with a magnetic sensor, and referring to the measurement data, the presence/absence of a damage in the inspection target and the location of the damage are determined.

However, measurement data obtained with the magnetic sensor with the magnetic field applying unit arranged only on the one side of the magnetic sensor has a weak magnetic field component derived from the inspection target. Thus, a change in the measurement data in accordance with the presence/absence of a damage in the inspection target is also small. It may therefore be difficult to read the change in accordance with the presence/absence of a damage in the inspection target from the measurement data.

SUMMARY

The present invention was made in view of the above problems in the conventional technology, and has an object to, in a magnetic non-destructive inspection, strengthen a magnetic field component derived from an inspection target by a new measurement method while following the measurement method of arranging a magnetic field applying unit only on one side of a magnetic sensor, thereby facilitating determination about the presence/absence of a damage in the inspection target and the location of the damage.

According to an aspect of the present invention, there is provided a measurement method of non-destructive inspection in which a magnetic material included in a non-magnetic body is an inspection target, the measurement method including:
  measuring that includes:
    application of a magnetic field of a first polarity that is an N polarity or an S polarity from a magnetic field applying unit to the inspection target at an application position through a surface of the non-magnetic body; and
    measurement of a magnetic field from the inspection target with a magnetic sensor on the surface of the non-magnetic body adjacent to the magnetic field applying unit at a plurality of positions having different distances from the magnetic field applying unit in a first direction away from the magnetic field applying unit, the inspection target forming a magnetic field distribution in which magnetic field is attenuated within a range of the first polarity with distance from the magnetic field applying unit, wherein
  the measuring includes first measuring and second measuring,
  in the first measuring, measurement is performed with the magnetic field applying unit arranged at an application position on one side in the first direction relative to the plurality of positions at which the magnetic sensor performs measurement, and
  in the second measuring, measurement is performed with the magnetic field applying unit arranged at an application position on a side other than the one side in the first direction relative to the plurality of positions at which the magnetic sensor performs measurement.

According to another aspect of the present invention, there is provided a measurement device of non-destructive inspection in which a magnetic material included in a non-magnetic body is an inspection target, the measurement device including:
  a magnetic field applying unit that applies a magnetic field; and
  a sensor unit that measures a magnetic field, wherein
  the magnetic field applying unit is attachable to and detachable from one end in a first direction of the sensor unit and is attachable to and detachable from another end other than the one end in the first direction of the sensor unit, and
  the sensor unit measures a magnetic field at a plurality of different positions that are at least along a first direction.

According to still another aspect of the present invention, there is provided a non-destructive inspection method in which a magnetic material included in a non-magnetic body is an inspection target, including:

acquiring of measurement data measured by applying a magnetic field of a first polarity that is an N polarity or an S polarity from a magnetic field applying unit to the inspection target through a surface of the non-magnetic body, and by measuring a magnetic field from the inspection target with a magnetic sensor on the surface of the non-magnetic body adjacent to the magnetic field applying unit at a plurality of positions having different distances from the magnetic field applying unit in a first direction away from the magnetic field applying unit, the inspection target forming a magnetic field distribution in which magnetic field is attenuated within a range of the first polarity with distance from the magnetic field applying unit; and calculating of determination data to determine a state of the inspection target based on the measurement data obtained in the acquiring, wherein in the acquiring, first measurement data and second measurement data are acquired, the first measurement data being measured with the magnetic field applying unit arranged at an application position on one side in the first direction relative to the plurality of positions at which the magnetic sensor performs measurement, and the second measurement data being measured with the magnetic field applying unit arranged at an application position on a side other than the one side in the first direction relative to the plurality of positions at which the magnetic sensor performs measurement, and in the calculating, the determination data is synthesized based on the first measurement data and the second measurement data.

According to still another aspect of the present invention, there is provided an information processing device of non-destructive inspection in which a magnetic material included in a non-magnetic body is an inspection target, the information processing device includes a hardware processor that:

acquires measurement data measured by applying a magnetic field of a first polarity that is an N polarity or an S polarity from a magnetic field applying unit to the inspection target through a surface of the non-magnetic body, and by measuring a magnetic field from the inspection target with a magnetic sensor on the surface of the non-magnetic body adjacent to the magnetic field applying unit at a plurality of positions having different distances from the magnetic field applying unit in a first direction away from the magnetic field applying unit, the inspection target forming a magnetic field distribution in which magnetic field is attenuated within a range of the first polarity with distance from the magnetic field applying unit; and calculates determination data to determine a state of the inspection target based on the measurement data obtained in acquiring the measurement data, wherein in acquiring the measurement data, the hardware processor acquires first measurement data and second measurement data, the first measurement data being measured with the magnetic field applying unit arranged at an application position on one side in the first direction relative to the plurality of positions at which the magnetic sensor performs measurement, and second measurement data being measured with the magnetic field applying unit arranged at an application position on the other side in the first direction relative to the plurality of positions at which the magnetic sensor performs measurement, and in calculating the determination data, the hardware processor synthesizes the determination data based on the first measurement data and the second measurement data.

According to still another aspect of the present invention, there is provided a non-transitory recording medium storing a computer readable program that causes a computer to function as an information processing device of non-destructive inspection in which a magnetic material included in a non-magnetic body is an inspection target, wherein the program causes the computer:

to acquire measurement data measured by applying a magnetic field of a first polarity that is an N polarity or an S polarity from a magnetic field applying unit to the inspection target through a surface of the non-magnetic body and by measuring a magnetic field from the inspection target with a magnetic sensor on the surface of the non-magnetic body adjacent to the magnetic field applying unit at a plurality of positions having different distances from the magnetic field applying unit in a first direction away from the magnetic field applying unit, the inspection target forming a magnetic field distribution in which the magnetic field is attenuated within a range of the first polarity with distance from the magnetic field applying unit;

to calculate determination data to determine a state of the inspection target based on the measurement data obtained in acquiring the measurement data;

in acquiring the measurement data, to acquire first measurement data and second measurement data, the first measurement data being measured with the magnetic field applying unit arranged at an application position on one side in the first direction relative to the plurality of positions at which the magnetic sensor performs measurement, and second measurement data being measured with the magnetic field applying unit arranged at an application position on the other side in the first direction relative to the plurality of positions at which the magnetic sensor performs measurement; and in calculating the determination data, to synthesize determination data based on the first measurement data and the second measurement data.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein.

DETAILED DESCRIPTION OF THE EMBODIMENTS

Hereinafter, an embodiment of the present invention will be described with reference to the drawings. The following describes an embodiment of the present invention and does not limit the present invention.

[Overview of Non-Destructive Inspection]

An overview of a non-destructive inspection according to an embodiment of the present invention will be described.

Figure 1:
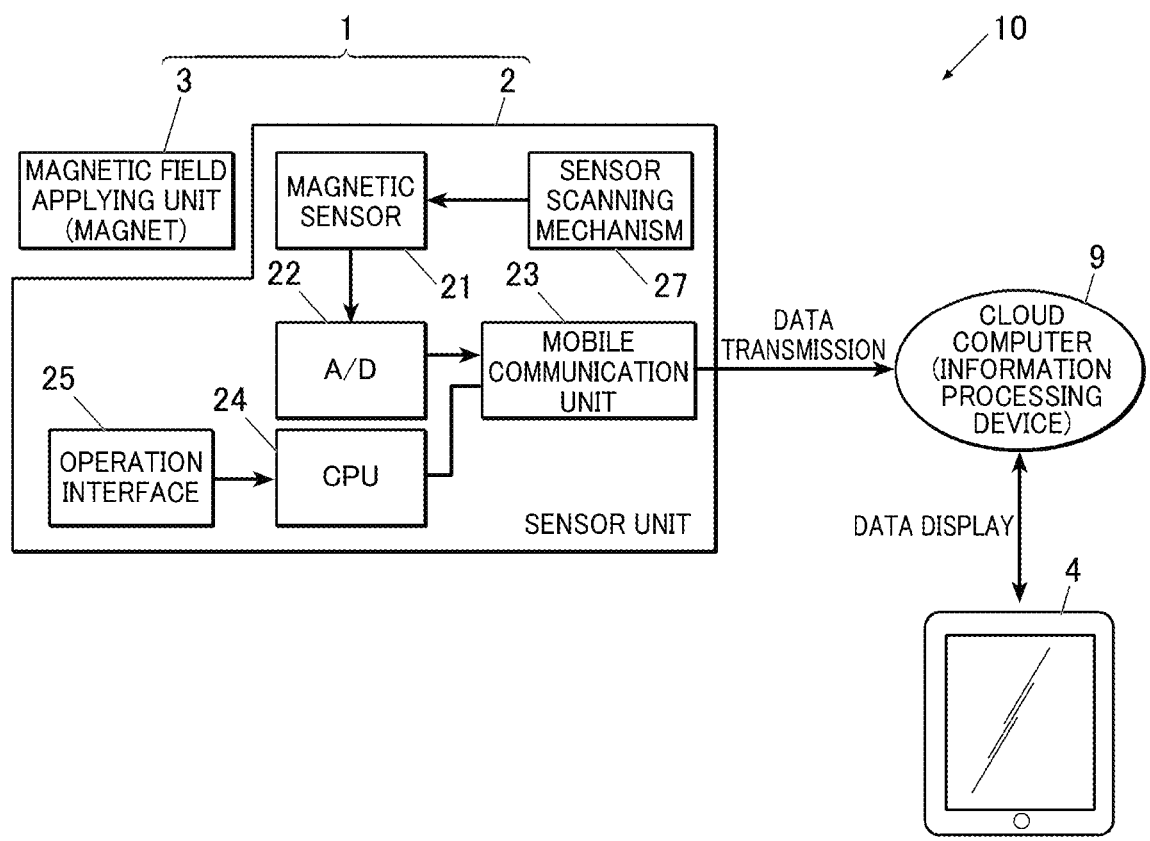
FIG. 1 is an overall configuration diagram of a non-destructive inspection system according to an embodiment of the present invention.

FIG. 1 shows an overall configuration diagram of a non-destructive inspection system according to the embodiment of the present invention.

As shown in FIG. 1, a non-destructive inspection system 10 according to the present embodiment includes a measurement device 1 for non-destructive inspection, a cloud computer 9, and a portable computer 4. The measurement device 1 includes a sensor unit 2 and a magnetic field applying unit 3. The sensor unit 2 is a block for magnetic measurement and has a plurality of magnetic sensors 21 mounted thereon. The magnetic sensors 21 may be single-axis sensors that sense a magnetic field component in a single-axis direction from an inspection target, but more preferably are three-axis sensors that sense magnetic fields in three-axis directions around the magnetic sensors. In the case of adopting the three-axis sensors as the magnetic sensors 21, three-axis sensors that sense magnetic field components in three-axis directions orthogonal to one another are preferable, but the magnetic sensors 21 may be configured by a combination of three single-axis sensors having sensor axes arranged in the three-axis directions, respectively.

Sensors such as a Hall element which is a semiconductor sensor, and an MR sensor, an MI sensor, and a TMR sensor which are magneto resistive sensors are known as the magnetic sensors 21. The present measurement device 1 employs a Hall element sensor in terms of a balance between magnetic sensitivity and dynamic range.

Measurement data generated by converting voltages produced by the magnetic sensors 21 into digital values in an A/D unit 22 is transmitted to the outside via a mobile communication unit 23.

The sensor unit 2 also includes an operation interface 25 in addition to a CPU 24 for overall control. The transmitted data is subjected to processing for inspection in the cloud computer 9 which is an example of an information processing device of the system of the present embodiment.

In this manner, the measurement device 1 outputs measurement data obtained by the sensor unit 2 to the outside. The form of outputting measurement data to the outside may be implemented by wired or wireless data communication, or by storing the measurement data in a recording medium that is attachable/detachable to/from the sensor unit 2.

In the present embodiment, the magnetic field applying unit 3 includes a permanent magnet.

In the present embodiment, the magnetic field applying unit 3 applies a magnetic field of either an N polarity or an S polarity to a magnetic body which is an inspection target, for example, an inspection target such as a steel material included in a non-magnetic body such as a concrete structure at an application position on a surface of the non-magnetic body, thereby forming a magnetic stream in the inspection target. The sensor unit 2 measures, with the magnetic sensors 21, magnetism leaked out of the inspection target in the state in which the magnetic stream is formed. This is called the Magnetic Stream Method.

The cloud computer 9 is a Web server, and immediately processes measurement data uploaded from the sensor unit 2 to enable the measurement data to be displayed on a browser application in the portable computer 4.

Figure 2A:
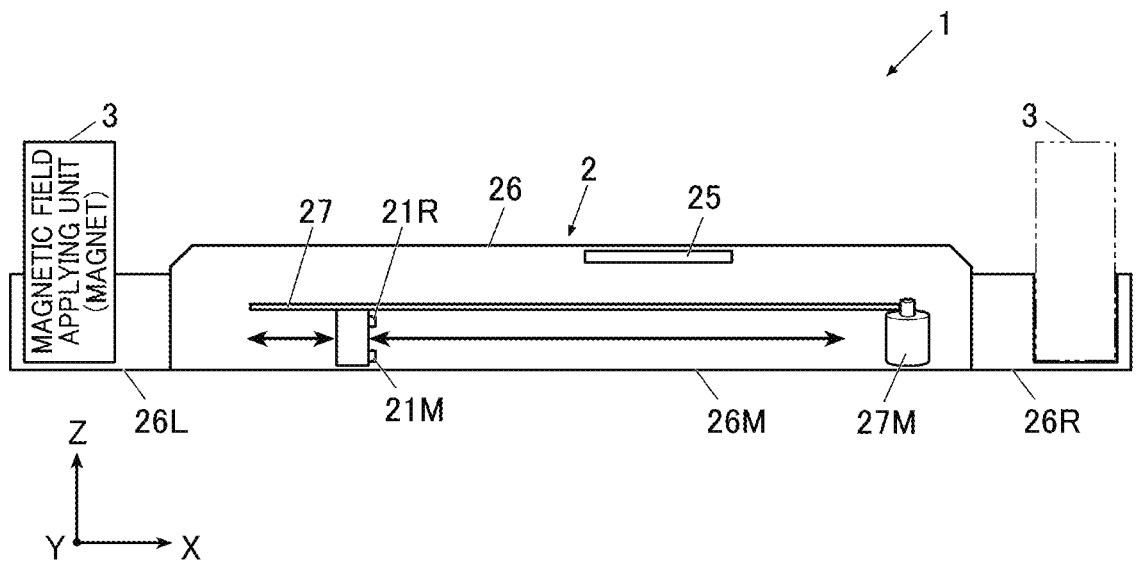
FIG. 2A is a schematic front view of a measurement device of non-destructive inspection according to the embodiment of the present invention, showing a state during first measurement.
Figure 2B:
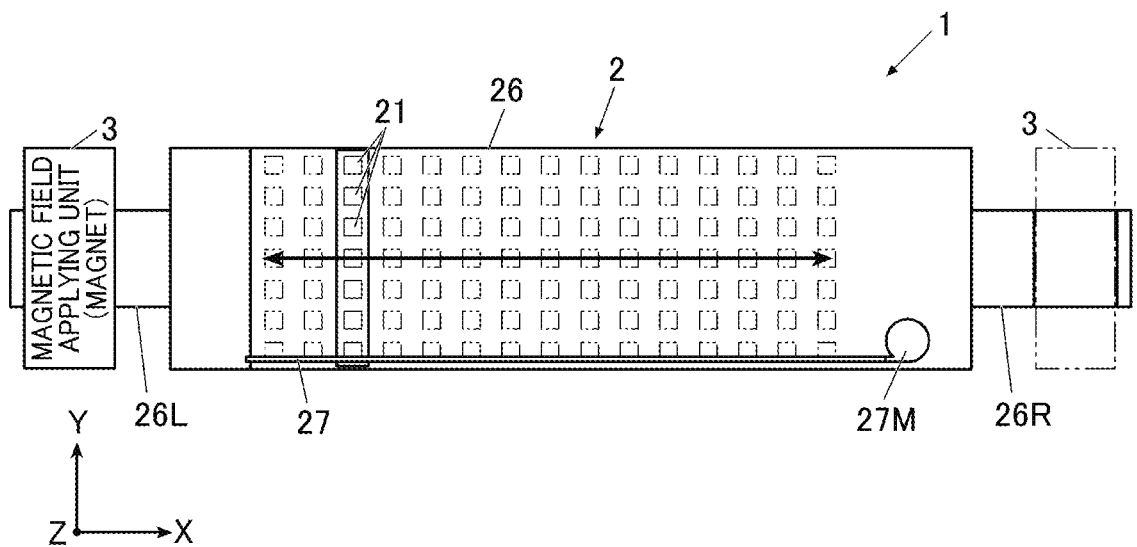
FIG. 2B is a schematic plan view of the measurement device of non-destructive inspection according to the embodiment of the present invention, showing the state during the first measurement.
Figure 3:
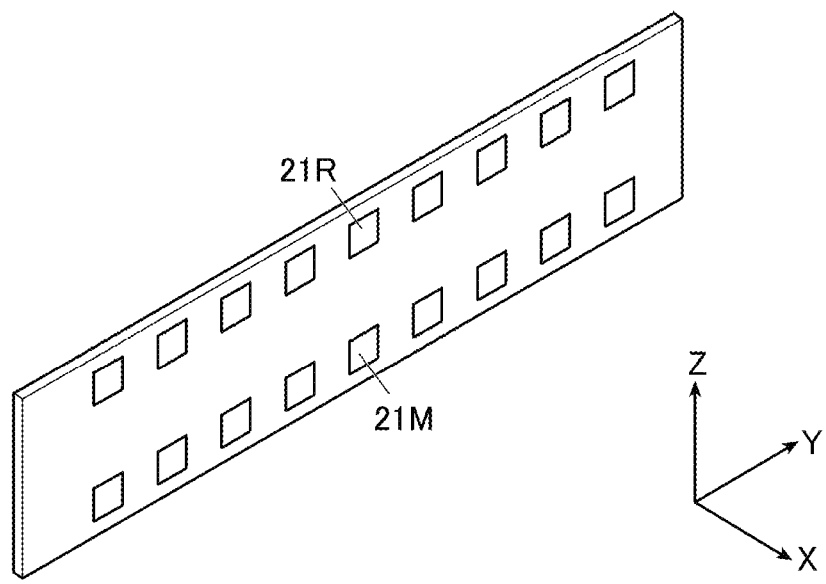
FIG. 3 is a perspective view of a sensor substrate according to the embodiment of the present invention.

FIGS. 2A, FIG. 2B, and FIG. 3 show mechanism diagrams of the measurement device of non-destructive inspection according to the present embodiment of the present invention.

As shown in FIG. 2A and FIG. 2B, a sensor array having one or more magnetic sensors 21 (21M, 21R) mounted thereon is arranged in an enclosure 26 proximate to a measurement surface 26M. The present embodiment mainly describes a case in which the sensor array is composed of a plurality of magnetic sensors 21. Orthogonal three axes XYZ are shown in the drawings where a first direction is the X-axis, a second direction is the Y-axis, and a third direction is the Z-axis.

As shown in FIG. 2A and FIG. 2B, the magnetic field applying unit 3 and the magnetic sensors 21 are arrayed in the first direction X. As shown in FIG. 2B, the plurality of magnetic sensors 21 are arrayed in the Y direction. As shown in FIG. 2A and FIG. 3, the two magnetic sensors 21M and 21R are arrayed in the Z direction. The measurement surface 26M is one of external surfaces of the enclosure 26 which is in parallel to the XY plane, on the side of which the magnetic sensors 21 are arranged proximately. In the opposite space in the enclosure 26, components such as a circuit substrate having the A/D unit 22, the mobile communication unit 23, the CPU 24, and the like described above in addition to the operation interface 25 mounted thereon are arranged. An end surface of the magnetic field applying unit 3 of the S polarity or the N polarity is arranged at substantially the same position on the Z-axis coordinate as the measurement surface 26M, and the magnetic field applying unit 3 is placed on the sensor unit 2. A holder 26L is provided on one end (a left end on the drawing) of the sensor unit 2 in the X direction in a manner coupled to the enclosure 26. A holder 26R is provided on the other end (a right end on the drawing) of the sensor unit 2 in the X direction in a manner coupled to the enclosure 26. The magnetic field applying unit 3 is attachable/detachable to/from the holders 26L and 26R. In this manner, for example, the magnetic field applying unit 3 is attachable/detachable to/from both the one end and the other end of the sensor unit 2 in the first direction X. By placing the magnetic field applying unit 3 in the holder 26L (26R), the magnetic field applying unit 3 is accurately arranged at an application position determined relative to the sensor unit 2. This enables the application position to be reproducibly settled at an accurate position regardless of operator skill.

The common attaching/detaching mechanism of the holder 26L on the one end and the holder 26R on the other end enables an identical magnetic field applying unit to be shared as the magnetic field applying unit 3 attachable/detachable to/from the holder 26L on the one end and the magnetic field applying unit 3 attachable/detachable to/from the holder 26R on the other end. This only requires the use of the single magnetic field applying unit 3, which simplifies the measurement device 1 and achieves more efficient measurement operation and management.

One of the two magnetic sensors 21M and 21R arrayed in the Z direction that is closer to the measurement surface 26M is the main sensor 21M, and the other on the farther side is the reference sensor 21R.

The sensor unit 2 performs scanning sensing of performing sensing while moving the magnetic sensors 21 with a sensor scanning mechanism 27 driven by a motor 27M in the X direction. In actual measurement, scanning sensing of the magnetic sensors 21 is executed in a state in which the measurement surface 26M of the enclosure 26 is installed on a to-be-measured surface (such as a concrete surface) of a measurement target structure including the inspection target. The sensor scanning mechanism 27 is configured to perform measurement while scanning the inspection target with the magnetic sensors 21 at any position and perform measurement with the magnetic sensors 21 stopped at any position unless installation positions of the sensor unit 2 and the magnetic field applying unit 3 are moved from fixed positions relative to the inspection target during measurement and perform measurement at the same position any number of times. The distance of the measurement position from the magnetic field applying unit 3 is reproducible.

The sensor unit 2 measures a magnetic field at a plurality of different positions in the first direction X in the above-described manner, for example. To achieve this, a sensor array type in which a plurality of magnetic sensors is arrayed in the X direction may be configured rather than the scanning type as described above. For example, the sensor unit 2 may be configured to have a plurality of magnetic sensors arrayed two-dimensionally in the first direction X and the second direction Y orthogonal to the first direction. This also enables measured values in the respective X and Y coordinates along the measurement surface 26M to be obtained.

The principles of measurement by the Magnetic Stream Method of the present invention will be described with reference to FIG. 4.

Figure 4:
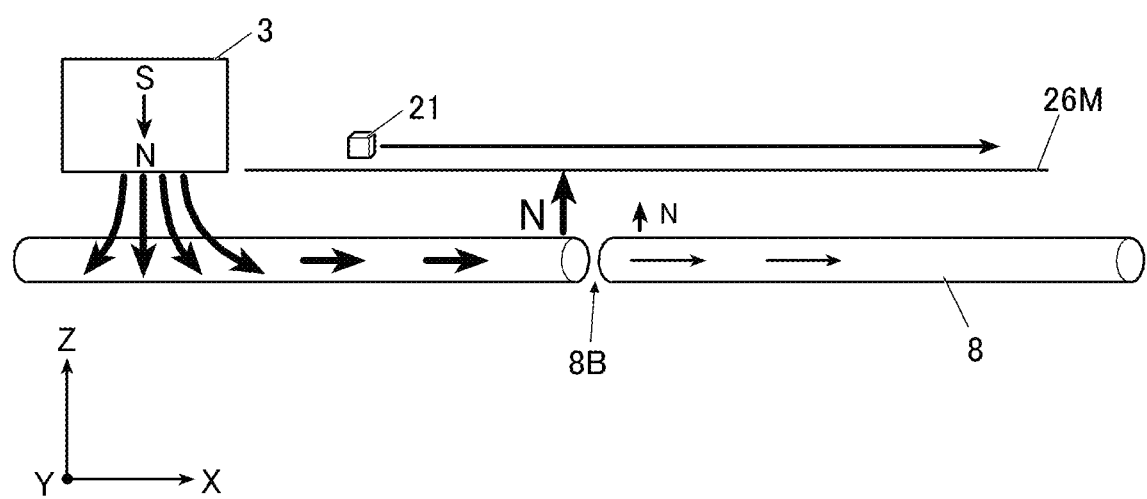
FIG. 4 is a state diagram of measurement performed by the Magnetic Stream Method according to the present invention.

FIG. 4 schematically shows a state in which a magnetic stream according to the measurement principles of the present invention has been formed.

An inspection target 8 is assumed to be a reinforcing steel rod or a PC steel material which is a magnetic material, and a state is assumed in which a broken part 8B which is a gap of about 1 cm has been created at a central part (a surrounding non-magnetic body (concrete) is not shown: the same applies hereinafter).

A magnetic field of the N polarity is applied from the magnetic field applying unit 3 to the inspection target 8, and magnetism flows through the inspection target 8 which is a magnetic body. Magnetism flowing through the magnetic body is discharged to the outside little by little and is gradually attenuated. The magnetic sensors 21 are configured to scan this inspection target 8 along the inspection target 8, and to capture a leakage magnetic flux in the longitudinal direction of the inspection target 8. The magnetic field applied from the magnetic field applying unit 3 to the inspection target 8 may have either the N polarity or the S polarity. In other words, the measurement device 1 according to the present embodiment is configured to apply a magnetic field of the first polarity which is the N polarity or the S polarity from the magnetic field applying unit 3 to the inspection target 8 adjacent in the third direction Z to the array of the magnetic field applying unit 3 and the magnetic sensors 21 in the first direction X, and sense, with the magnetic sensors 21, a magnetic field from the inspection target 8 in a state in which a magnetic field distribution that the magnetic field is attenuated within the range of the first polarity with distance from the magnetic field applying unit 3 in the first direction X is formed. Then, the magnetic field is measured with the magnetic sensors 21 at a plurality of positions having different distances from the magnetic field applying unit 3 in the first direction X, and a magnetic field distribution in the first direction X in accordance with the distances from the magnetic field applying unit 3 is obtained. By using the above-described scanning type or sensor array type sensor unit 2, the magnetic field distribution in the first direction X in accordance with the distances from the magnetic field applying unit 3 is obtained.

Herein, if the inspection target 8 has no breakage, a leakage magnetic force is gradually weakened with distance from the magnetic field applying unit 3. If the inspection target 8 has the broken part 8B as shown in FIG. 4, the flow of magnetism is cut off at the broken part 8B. A large part of the magnetism is discharged in front of the broken part 8B accordingly, so that magnetism flowing to the inspection target 8 beyond the broken part 8B is reduced. The measurement device 1 enables a difference between distributions of leakage magnetic fluxes of the inspection target 8 in accordance with the presence/absence of a breakage to be captured.

Figure 5:
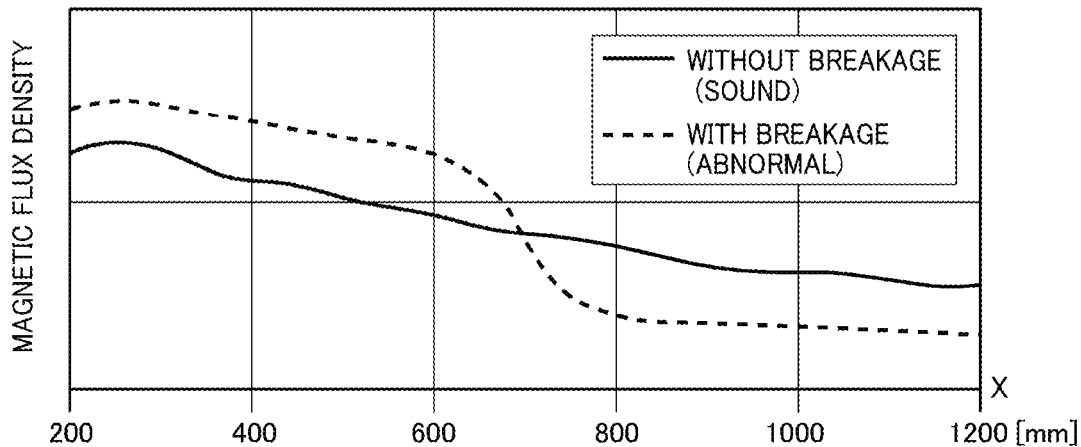
FIG. 5 is an example of a measured waveform diagram of magnetic field distributions of a Z-direction magnetic field component in a first direction X.

FIG. 5 shows an example of a measured waveform diagram of magnetic field distributions in the first direction X.

Figure 6:
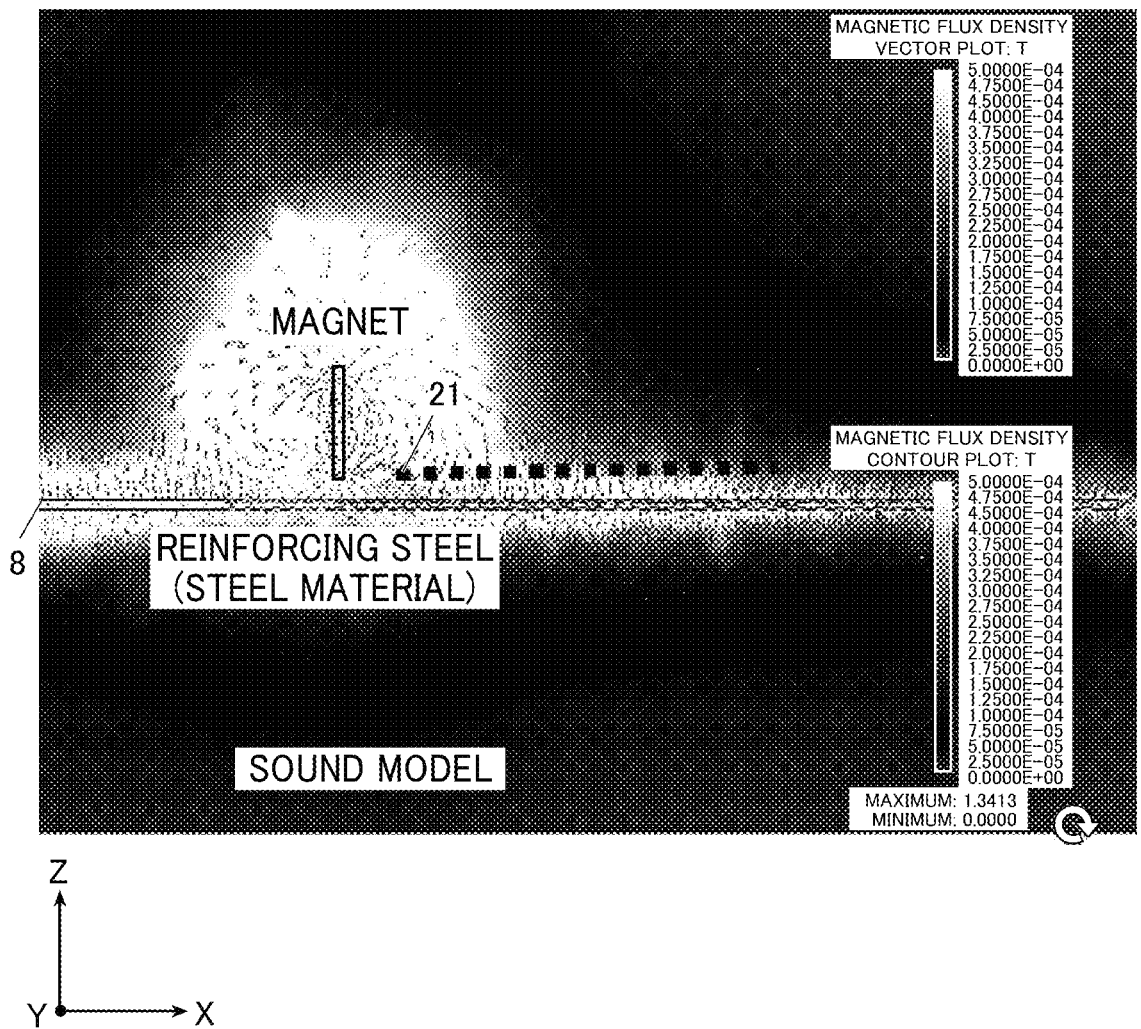
FIG. 6 is a two-dimensional distribution diagram of a magnetic field on an X-Z plane measured for a sound model.
Figure 7:
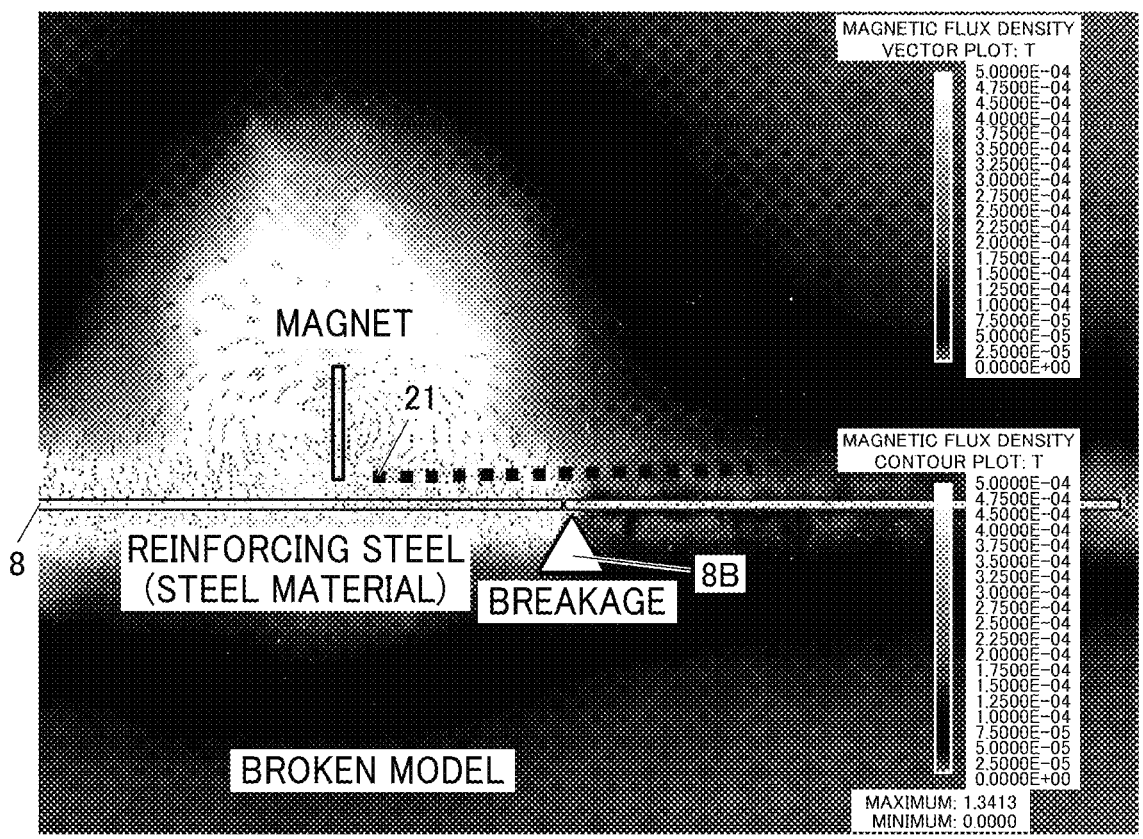
FIG. 7 is a two-dimensional distribution diagram of a magnetic field on the X-Z plane measured for a broken model.

FIG. 5 is obtained by capturing distributions of a Z-direction magnetic field component on the XY plane away from the inspection target 8 by a certain distance in the Z direction with the magnetic sensors 21, for two conditions of a case (broken model) in which the inspection target has a breakage at a central part as shown in FIG. 4 and a sound case (sound model) in which the inspection target 8 has no breakage. FIG. 6 shows a two-dimensional distribution diagram (obtained by converting a color heat map into gray scale) of a magnetic field on the XZ plane measured separately for the sound model, and FIG. 7 shows a two-dimensional distribution diagram of a magnetic field on the XZ plane measured separately for the broken model. In FIG. 6 and FIG. 7, a whiter portion indicates a portion with a stronger magnetic field, and black squares indicate measurement positions of the magnetic sensors 21.

As described earlier, in the case in which the inspection target 8 has no breakage, a magnetic force applied by the magnetic field applying unit 3 arranged on the left side of the inspection target 8 in FIG. 4 is discharged to the outside while being attenuated little by little during the flow through the inspection target 8 in the Y direction and (see the solid graph in FIG. 5 and FIG. 6).

In the case in which the inspection target 8 has a breakage at the central part, a magnetic force applied by the magnetic field applying unit 3 is discharged to the outside while being attenuated little by little until reaching the broken part 8B during the flow through the inspection target 8 in the Y direction, but the stream flowing through the inspection target 8 is cut off at the broken part 8B. Thus, the magnetic force hardly flows across the broken part 8B, resulting in a waveform in which the magnetic field is sharply attenuated at the broken part 8B (see the broken line graph in FIG. 5 and FIG. 7). Conversely, another feature caused by the breakage is that a large part of magnetism is discharged in front of the broken part 8B, so that a measured value in the case in which the breakage is present on the near side of the broken part 8B in the left region in the drawing exceeds a measured value in the case in which there is no breakage. The above tendency of magnetic field distributions in accordance with the presence/absence of a breakage also holds in magnetic field distributions at the measurement positions (black squares) of the magnetic sensors 21 in FIG. 6 and FIG. 7. When monitoring magnetic field distributions at the measurement positions (black squares) of the magnetic sensors 21 in the X direction away from the magnet, the magnetic field is attenuated at a substantially constant decrease rate in the sound model of FIG. 6, while in the broken model of FIG. 7, the magnetic field is strengthened in front of the broken part 8B, and conversely, sharply attenuated beyond the broken part 8B. Consequently, it is appreciated that the magnetic field distributions as shown in FIG. 5 are measured with the magnetic sensors 21 away from the inspection target 8 in the Z direction.

[Measurement and Subsequent Processing]

Figure 8:
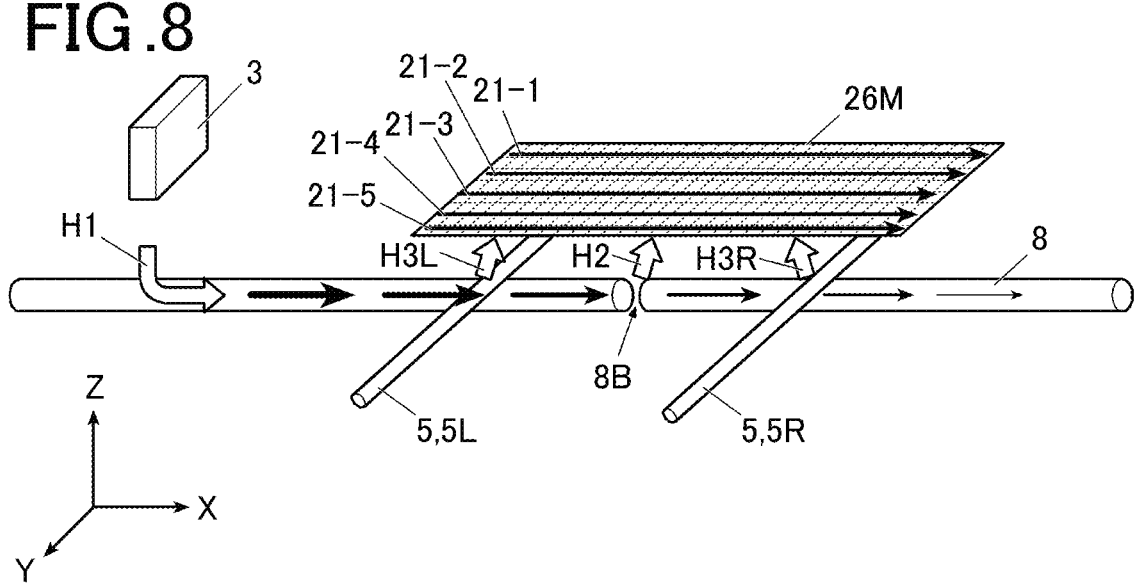
FIG. 8 is a state diagram of measurement in a case in which crossing stirrups are provided.

Herein, elements shown in FIG. 8 are assumed as conditions during measurement.

The inspection target 8 such as a PC steel material and the crossing stirrups 5 are included in a non-magnetic material such as concrete. The crossing stirrups 5 are magnetic materials other than the inspection target 8.

The magnetic field applying unit 3 is placed on the surface of the non-magnetic material, and a magnetic field (H1) is applied to the inspection target 8. Measurement is performed with the magnetic sensors 21 while moving away from the magnetic field applying unit 3 in the longitudinal direction (the X direction) of the inspection target 8. In this example, a configuration in which five magnetic sensors (21-1 to 21-5) are arrayed in the Y direction as illustrated is adopted, but any number of magnetic sensors may be provided.

The crossing stirrups 5 are located between the surface of the non-magnetic material on which the measurement surface 26M is arranged and the inspection target 8 and extend in the Y direction. A plurality of the crossing stirrups 5 are arrayed in the X direction.

Figure 9:
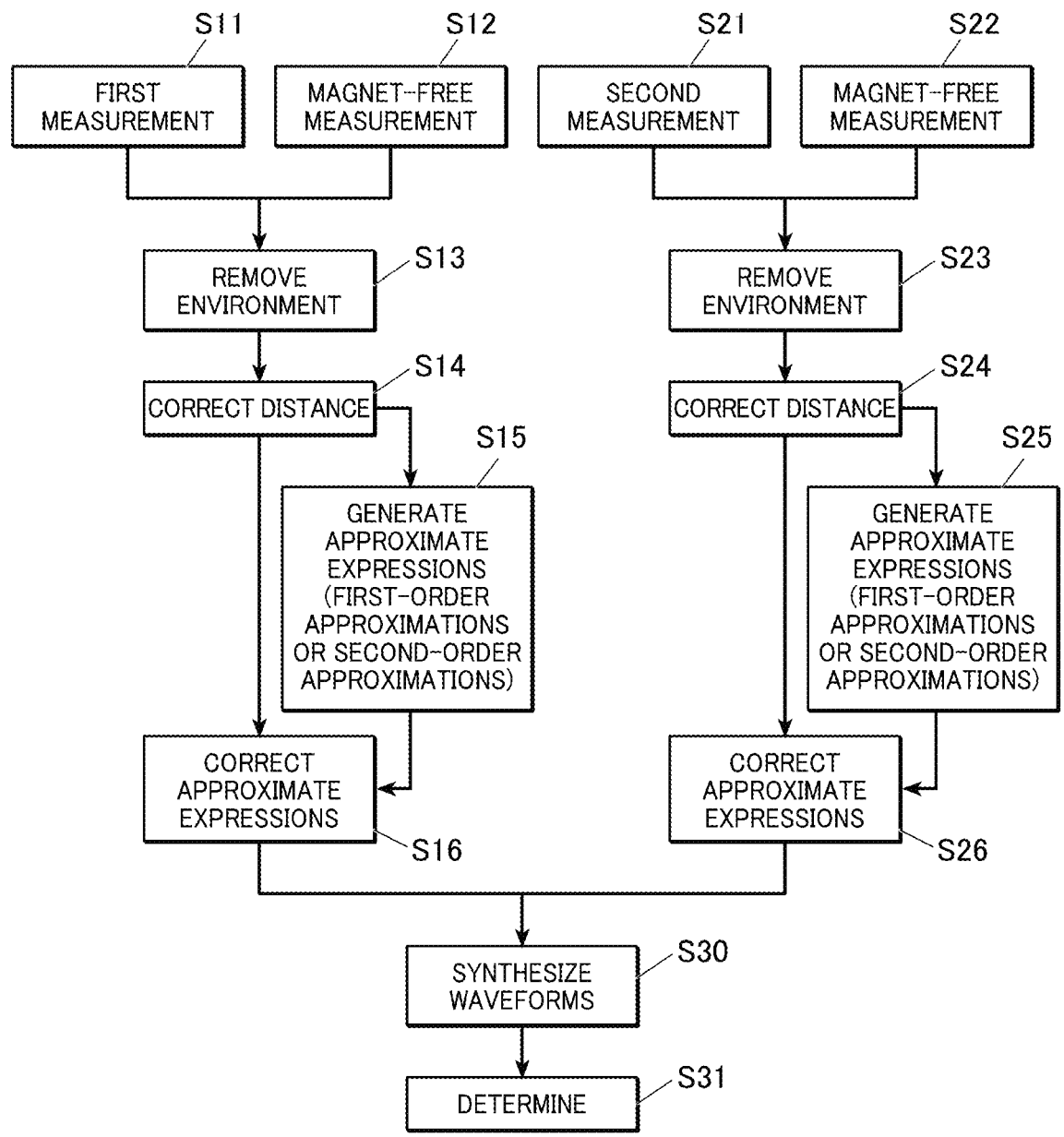
FIG. 9 is a flowchart showing measurement and subsequent processing according to the embodiment of the present invention.

The flowchart of FIG. 9 is referred to for measurement and subsequent processing.

(Measurement Stage)

First measurement step S11 is performed first.

In first measurement step S11, measurement is executed with the measurement device 1 in which the magnetic field applying unit 3 has been placed in the holder 26L as shown in FIG. 2.

In first measurement step S11, measurement is performed with the magnetic field applying unit 3 arranged at an application position (the holder 26L) on one side in the X direction relative to a plurality of positions in the X direction at which measurement is performed with the magnetic sensors 21. Data thereby acquired is called first measurement data.

Two-dimensional distribution data on the XY plane is obtained by the measurement device 1. In the respective coordinates, respective measured values of an X-direction magnetic field component, a Y-direction magnetic field component, and a Z-direction magnetic field component are obtained.

Figure 12A:
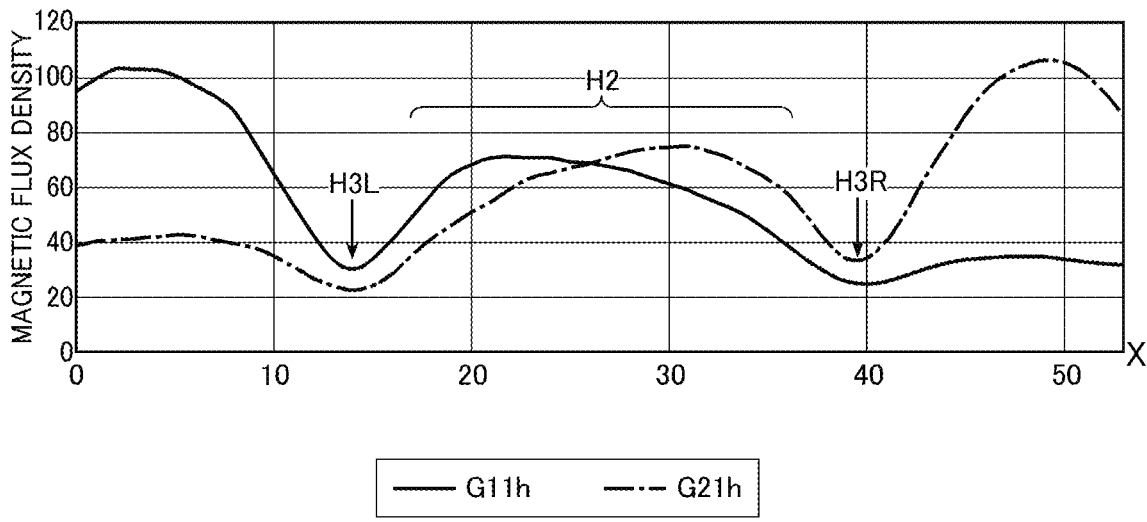
FIG. 12A is a graph showing an example of first measurement data and second measurement data after environment removing processing in a case in which an inspection target is sound.

An example graph G11$h$ shown in FIG. 12A is equivalent to the first measurement data and is a distribution graph of the Z-direction magnetic field component with the X-axis serving as the horizontal axis, showing the case in which the inspection target 8 is sound. However, data after environment removal step S13 which will be described later is shown.

Figure 12B:
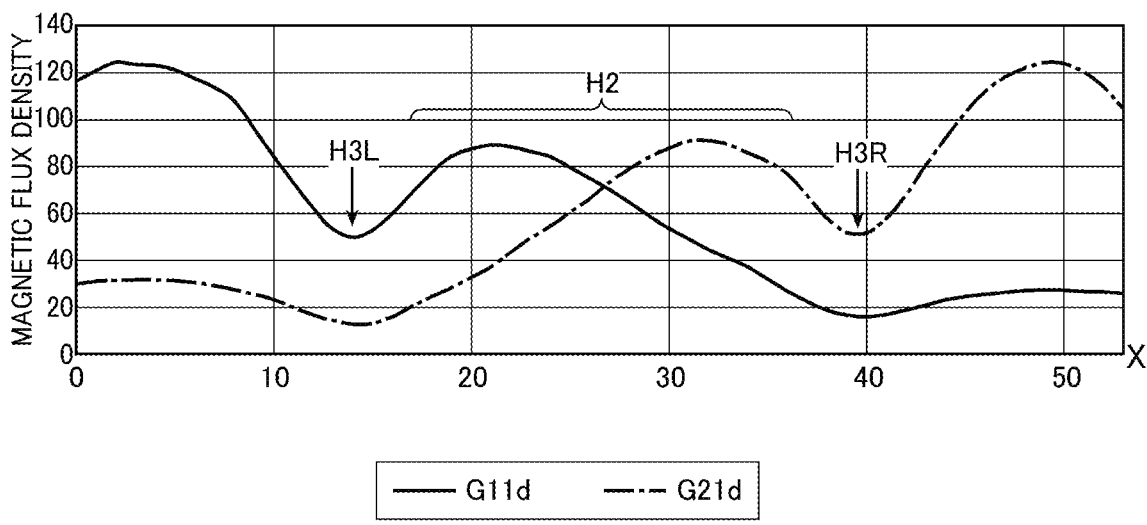
FIG. 12B is a graph showing an example of the first measurement data and the second measurement data after the environment removing processing in a case in which the inspection target has a breakage.

An example graph G11$d$ shown in FIG. 12B is equivalent to the first measurement data and is a distribution graph of the Z-direction magnetic field component with the X-axis serving as the horizontal axis, showing the case in which the inspection target 8 has a breakage. However, data after environment removal step S13 which will be described later is shown.

Next, magnet-free measurement step S12 is performed.

Figure 10:
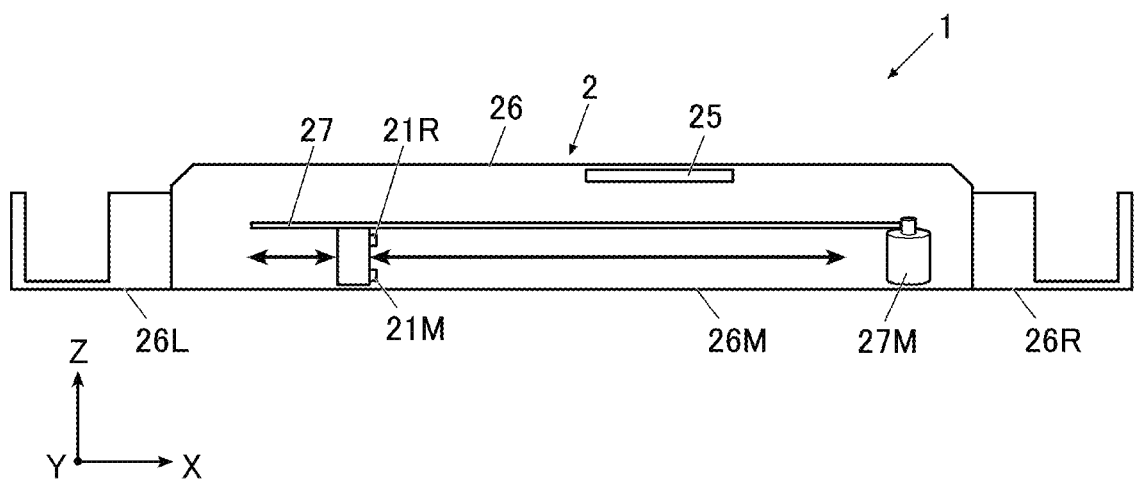
FIG. 10 is a schematic front view of the measurement device of non-destructive inspection according to the embodiment of the present invention, showing a state during magnet-free measurement.

In magnet-free measurement step S12, measurement is performed under a condition where the magnetic field applying unit 3 in first measurement step S11 is detached and removed from the holder 26L as shown in FIG. 10, so that the magnetic field applied to the inspection target 8 by the magnetic field applying unit 3 is excluded. The condition is that measurement is performed in a state in which the influence of application of the magnetic field by the magnetic field applying unit 3 in first measurement step S11 remains. Measurement data thereby measured is called complementary measurement data.

The complementary measurement data measured in magnet-free measurement step S12 is equivalent to measurement data measured in the state in which the magnetic field applying unit 3 has been removed from the application position (the holder 26L) on the one side after the first measurement data is measured.

On the other hand, second measurement step S21 is performed.

Figure 11:
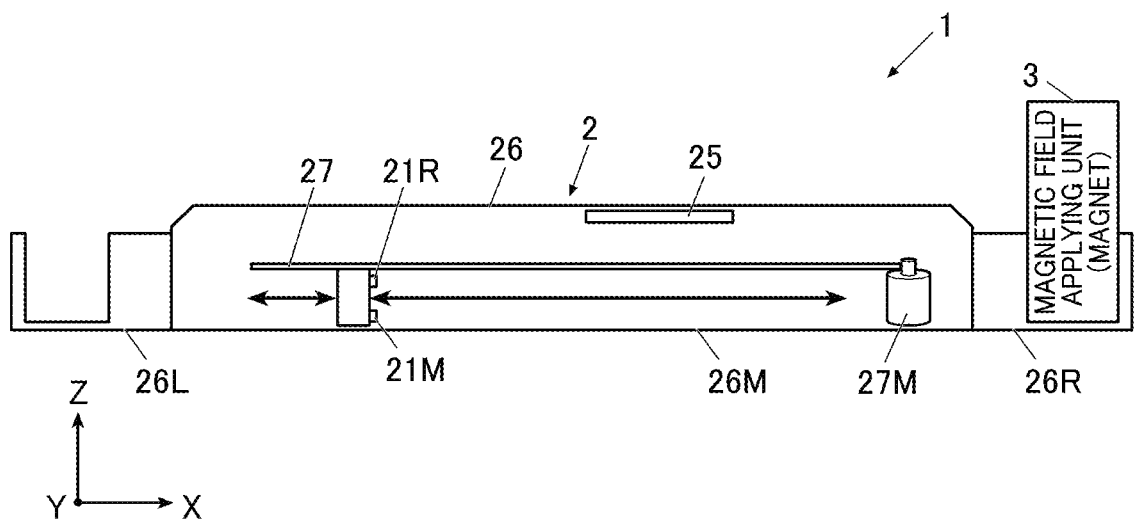
FIG. 11 is a schematic front view of the measurement device of non-destructive inspection according to the embodiment of the present invention, showing a state during second measurement.

In second measurement step S21, measurement is executed with the measurement device 1 in which the magnetic field applying unit 3 has been placed in the holder 26R as shown in FIG. 11. The order of first measurement step S11 and second measurement step S21 is not limited. The sensor unit 2 shall not be moved relative to the inspection target 8 in first measurement step S11, second measurement step S21, and magnet-free measurement steps S12 and S22 in order to obtain measurement data at identical positions.

In second measurement step S21, measurement is performed with the magnetic field applying unit 3 arranged at an application position (the holder 26R) on the other side in the X direction relative to the plurality of positions in the X direction at which measurement is performed with the magnetic sensors 21. Data thereby acquired is called second measurement data.

An example graph G21h shown in FIG. 12A is equivalent to the second measurement data and is a distribution graph of the Z-direction magnetic field component with the X-axis serving as the horizontal axis, showing the case in which the inspection target 8 is sound. However, data after environment removal step S23 which will be described later is shown.

An example graph G21d shown in FIG. 12B is equivalent to the second measurement data and is a distribution graph of the Z-direction magnetic field component with the X-axis serving as the horizontal axis, showing the case in which the inspection target 8 has a breakage. However, data after environment removal step S23 which will be described later is shown.

Next, magnet-free measurement step S22 is performed.

In magnet-free measurement step S22, measurement is performed under a condition where the magnetic field applying unit 3 in second measurement step S21 is detached and removed from the holder 26R as shown in FIG. 10, so that the magnetic field applied to the inspection target 8 by the magnetic field applying unit 3 is excluded. The condition is that measurement is performed in a state in which the influence of application of the magnetic field by the magnetic field applying unit 3 in second measurement step S21 remains. Measurement data thereby measured is called complementary measurement data.

The complementary measurement data measured in magnet-free measurement step S22 is equivalent to measurement data measured in the state in which the magnetic field applying unit 3 has been removed from the application position (the holder 26R) on the other side after the second measurement data is measured. The application position on the one side and the application position on the other side may correspond to either the holder 26L or the holder 26R.

Regardless of the above description of steps S11, S12, S21, and S22, magnet-free measurement steps S12 and S22 may be made common and may be carried out before or after steps S11 and S21.

The first measurement data, the second measurement data, and the complementary measurement data measured with the measurement device 1 as described above are output to the outside and acquired by the cloud computer 9.

In other words, the measurement device 1 outputs, to the outside, the first measurement data measured with the sensor unit 2 in the state in which the magnetic field applying unit 3 is arranged on the one end in the X direction and not arranged on the other end, the second measurement data measured with the sensor unit 2 in the state in which the magnetic field applying unit 3 is arranged on the other end and not arranged on the one end, and the complementary measurement data measured in the state in which the magnetic field applying unit 3 has been removed.

(Processing Stage after Measurement)

The cloud computer 9 functions as a measurement data acquirer and a determination data calculator based on an information processing program for non-destructive inspection and executes a measurement data acquisition step and a determination data calculation step.

First, the cloud computer 9 serves as the measurement data acquirer to receive the first measurement data, the second measurement data, and the complementary measurement data, thereby completing the measurement data acquisition step.

Next, the cloud computer 9 serves as the determination data calculator to execute the determination data calculation step (S13-16, S23-26, S30) of calculating determination data for determining the state of the inspection target 8 based on the measurement data acquired in the measurement data acquisition step.

As the determination data calculation step, environment removal steps S13 and S23 are executed first.

In environment removal step S13, the complementary measurement data measured in magnet-free measurement step S12 is subtracted from the first measurement data. In environment removal step S23, the complementary measurement data measured in magnet-free measurement step S22 is subtracted from the second measurement data. Herein, in the case in which magnet-free measurement steps S12 and S22 are made common, the complementary measurement data to be subtracted from the first measurement data and the complementary measurement data to be subtracted from the second measurement data are identical.

Environment removal steps S13 and S23 enable a noise component not derived from the magnetic field applying unit 3 but derived from an environmental magnetic field to be removed from the measurement data and enable a signal component that varies depending on the state of the inspection target 8 to be easily read.

Next, distance correction steps S14 and S24 are executed.

In distance correction step S14, the first measurement data is subjected to a distance correction of decreasing reduction in the magnetic field in accordance with the distance from the magnetic field applying unit 3 on the one side (the holder 26L). In distance correction step S24, the second measurement data is subjected to a distance correction of decreasing reduction in the magnetic field in accordance with the distance from the magnetic field applying unit 3 on the other side (the holder 26R).

In other words, correction of strengthening a signal is performed as the distance is larger. As a method therefor, a calculation of multiplying a measured value at a distance by N-th power of the distance is performed. At this time, N should range from 1.0 to 4.0.

As the distance from the magnetic field applying unit 3 is larger, the amount of correction is increased. A correction factor P is expressed as $P(x)=(x/x1)^N$ as a function of x where the X coordinate of the magnetic field applying unit 3 is the origin 0, an X coordinate of a measurement position closest to the magnetic field applying unit 3 is x1, and an X coordinate of each measurement position is x, for example. At this time, a distance correction shall be conversion of a measured value on each X coordinate to $P(x)$ times.

Figure 13A:
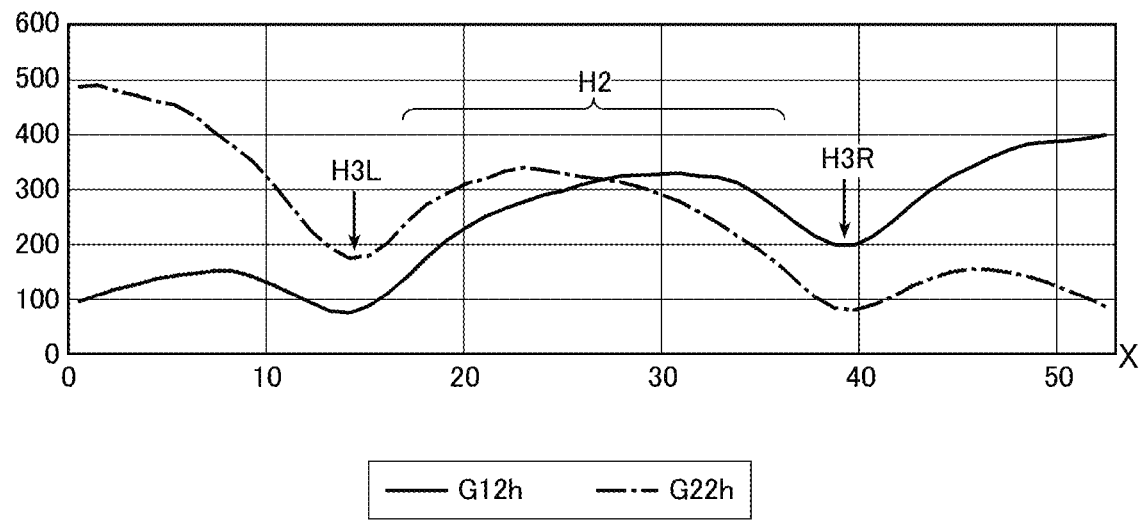
FIG. 13A and FIG. 13B are graphs equivalent to the data in FIG. 12A and FIG. 12B after di stance corrections.
Figure 13B:
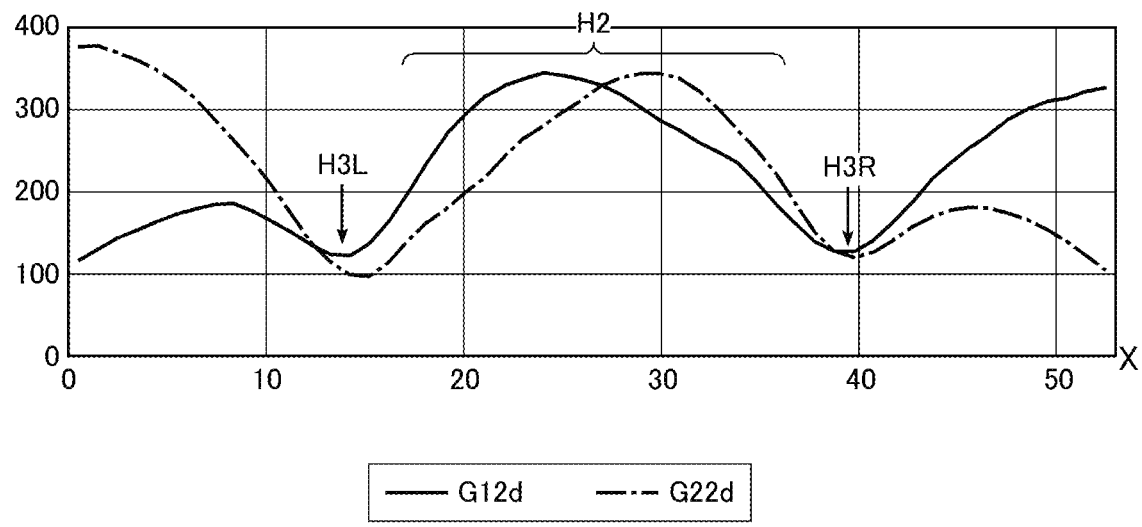

Graphs after distance correction steps S14 and S24 are shown in FIG. 13A and FIG. 13B. The distance correction changes the graph G11h to a graph G12h, the graph G21h to a graph G22h, the graph G11d to a graph G12d, and the graph G21d to a graph G22d.

As shown in FIG. 13A and FIG. 13B, reduction in the signal is decreased in accordance with the distance.

Distance correction steps S14 and S24 decrease a component that varies in accordance with the distance from the magnetic field applying unit 3 and enable a signal component that varies depending on the state of the inspection target 8 to be easily read.

Next, approximate expression generation steps S15 and S25 are executed.

Figure 14A:
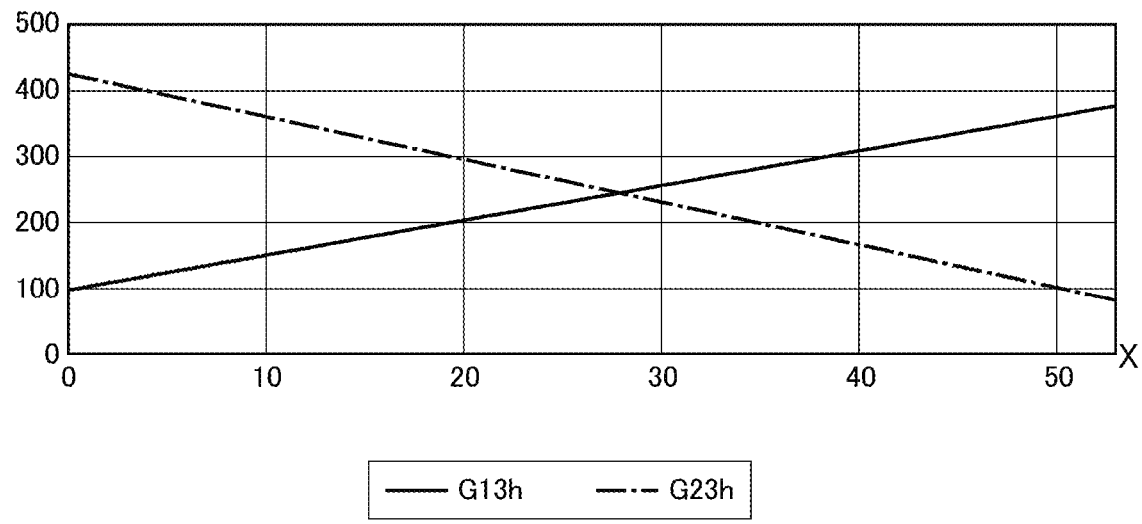
FIG. 14A and FIG. 14B are graphs equivalent to first-order approximate expressions of the data shown in FIG. 13A and FIG. 13B.
Figure 14B:
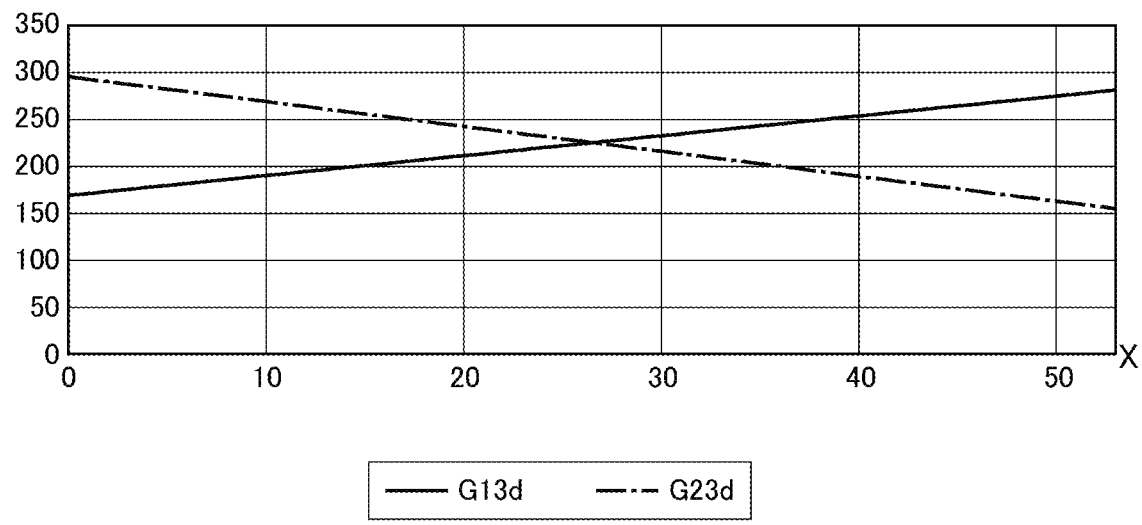
Figure 15A:
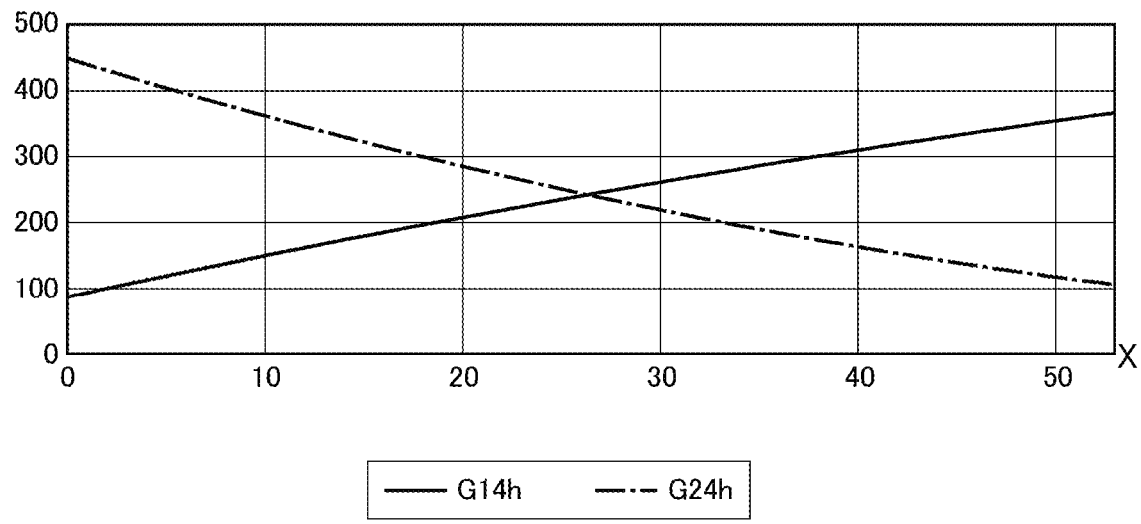
FIG. 15A and FIG. 15B are graphs equivalent to second-order approximate expressions of the data shown in FIG. 13A and FIG. 13B.
Figure 15B:
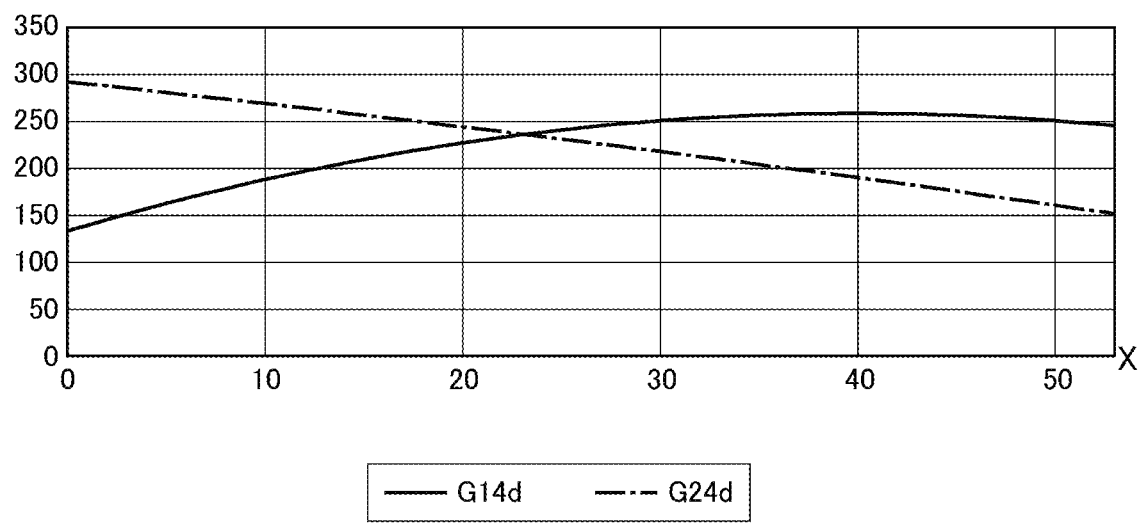

In approximate expression generation step S15, first-order approximate expressions or second-order approximate expressions are calculated for the first measurement data. This calculation is performed for the first measurement data after the environment removal processing and the distance correction. Graphs of the calculated first-order approximate expressions are shown in FIG. 14A and FIG. 14B. A graph G13h is a graph of the first-order approximate expression calculated for the graph G12h. A graph G13d is a graph of the first-order approximate expression calculated for the graph G12d. Graphs of the calculated second-order approximate expressions are shown in FIG. 15A and FIG. 15B. A graph G14h is a graph of the second-order approximate expression calculated for the graph G12h. A graph G14d is a graph of the second-order approximate expression calculated for the graph G12d.

In approximate expression generation step S25, first-order approximate expressions or second-order approximate expressions are calculated for the second measurement data. This calculation is performed for the second measurement data after the environment removal processing and the distance correction. Graphs of the calculated first-order approximate expressions are shown in FIG. 14A and FIG. 14B. A graph G23h is a graph of the first-order approximate expression calculated for the graph G22h. A graph G23d is a graph of the first-order approximate expression calculated for the graph G22d. Graphs of the calculated second-order approximate expressions are shown in FIG. 15A and FIG. 15B. A graph G24h is a graph of the second-order approximate expression calculated for the graph G22h. A graph G24d is a graph of the second-order approximate expression calculated for the graph G22d.

The first-order approximate expressions or the second-order approximate expressions may be selectively calculated.

Next, approximate expression correction steps S16 and S26 are executed.

In approximate expression correction step S16, the values of the approximate expressions obtained in approximate expression generation step S15 are subtracted from the first measurement data.

Figure 16A:
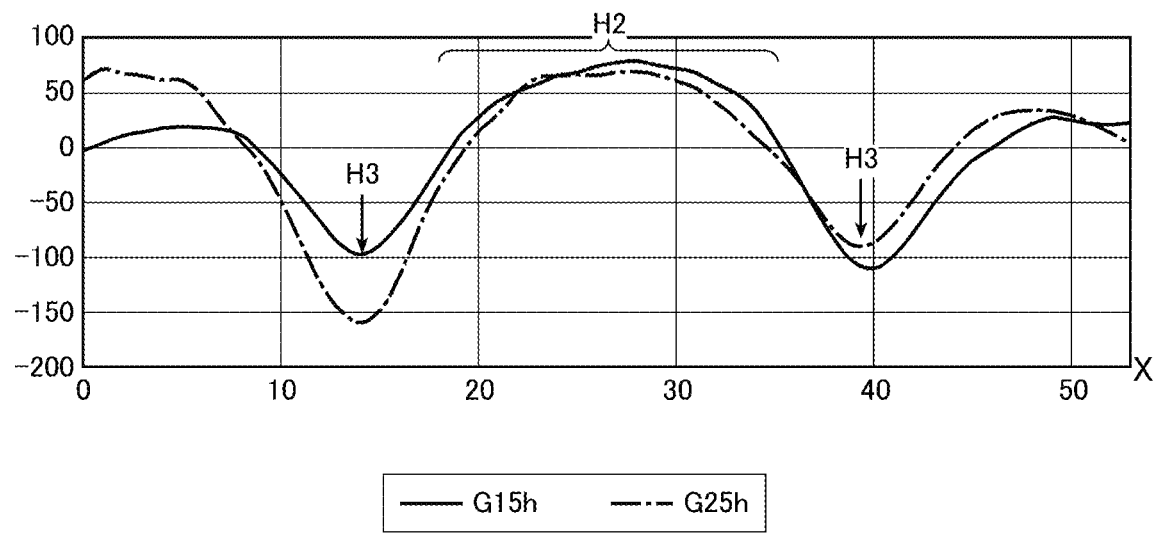
FIG. 16A and FIG. 16B are graphs equivalent to the data shown in FIG. 13A and FIG. 13B after correction processing using the first-order approximate expressions shown in FIG. 14A and FIG. 14B.
Figure 16B:
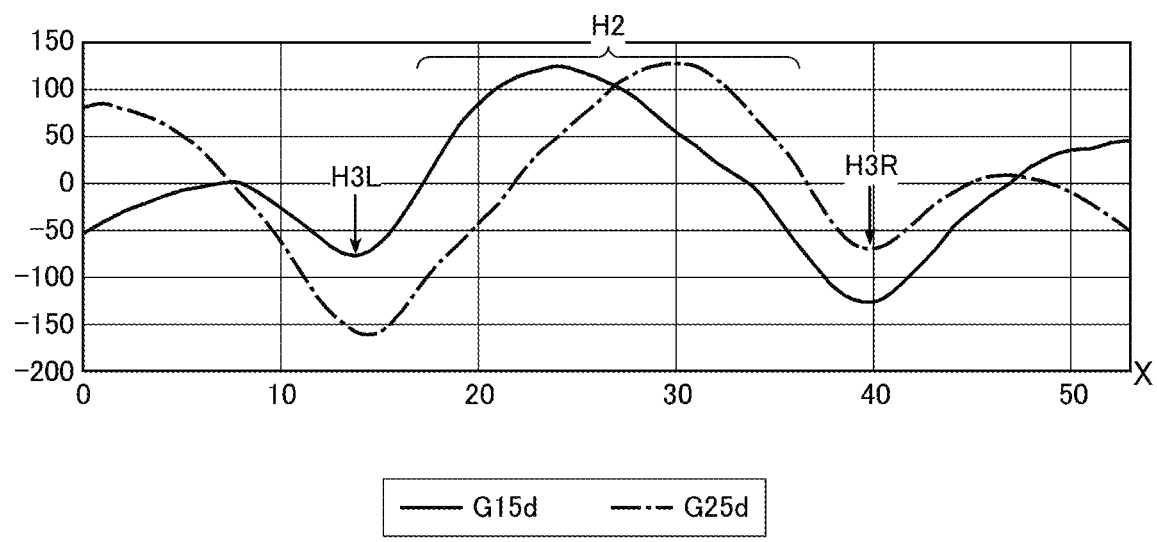

In the case of the first-order approximate expressions, a calculation of subtracting, from a measured value in the graph G12h, a measured value on the same X coordinate in the graph G13h to obtain a graph G15h shown in FIG. 16A is performed. Similarly, a calculation of subtracting, from a measured value in the graph G12d, a measured value on the same X coordinate in the graph G13d to obtain a graph G15d shown in FIG. 16B is performed.

Figure 17A:
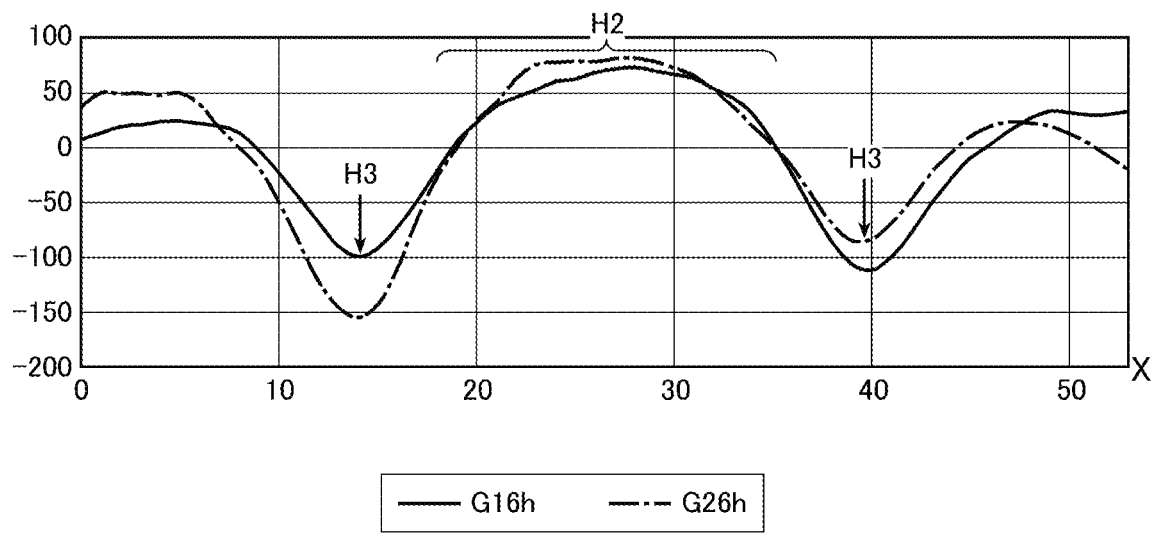
FIG. 17A and FIG. 17B are graphs equivalent to the data shown in FIG. 13A and FIG. 13B after correction processing using the second-order approximate expressions shown in FIG. 15A and FIG. 15B.
Figure 17B:
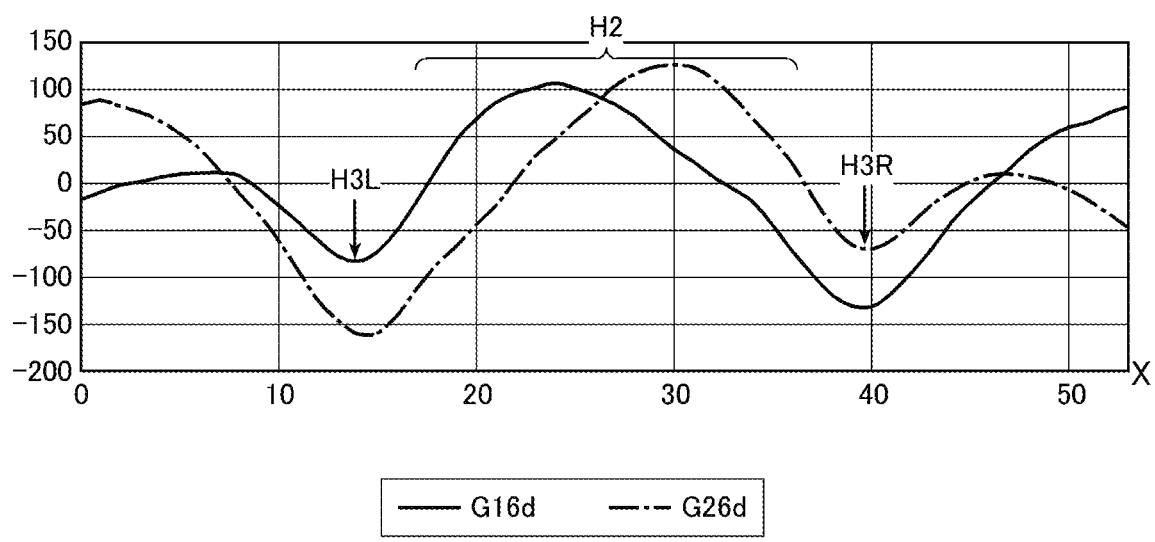

In the case of the second-order approximate expressions, a calculation of subtracting, from a measured value in the graph G12h, a measured value on the same X coordinate in the graph G14h to obtain a graph G16h shown in FIG. 17A is performed. Similarly, a calculation of subtracting, from a measured value in the graph G12d, a measured value on the same X coordinate in the graph G14d to obtain a graph G16d shown in FIG. 17B is performed.

In approximate expression correction step S26, values of the approximate expressions obtained in approximate expression generation step S25 are subtracted from the second measurement data.

In the case of the first-order approximate expressions, a calculation of subtracting, from a measured value in the graph G22h, a measured value on the same X coordinate in the graph G23h to obtain a graph G25h shown in FIG. 16A is performed. Similarly, a calculation of subtracting, from a measured value in the graph G22d, a measured value on the same X coordinate in the graph G23d to obtain a graph G25d shown in FIG. 16B is performed.

In the case of the second-order approximate expressions, a calculation of subtracting, from a measured value in the graph G22h, a measured value on the same X coordinate in the graph G24h to obtain a graph G26h shown in FIG. 17A is performed. Similarly, a calculation of subtracting, from a measured value in the graph G22d, a measured value on the same X coordinate in the graph G24d to obtain a graph G26d shown in FIG. 17B is performed.

As shown in FIG. 16A to FIG. 17B, the right upward inclination or the left upward inclination of the whole graph is resolved by approximate expression correction steps S16 and S26, which enables a signal component that varies depending on the state of the inspection target 8 to be easily read. This enables the inclination of the whole graph that cannot be resolved by the above-described distance corrections to be resolved.

Next, waveform synthesis step S30 is executed.

In waveform synthesis step S30, determination data is synthesized based on the first measurement data after executing approximate expression correction step S16 and the second measurement data after executing approximate expression correction step S26. Herein, difference calculation is executed as synthesis calculation.

Figure 18:
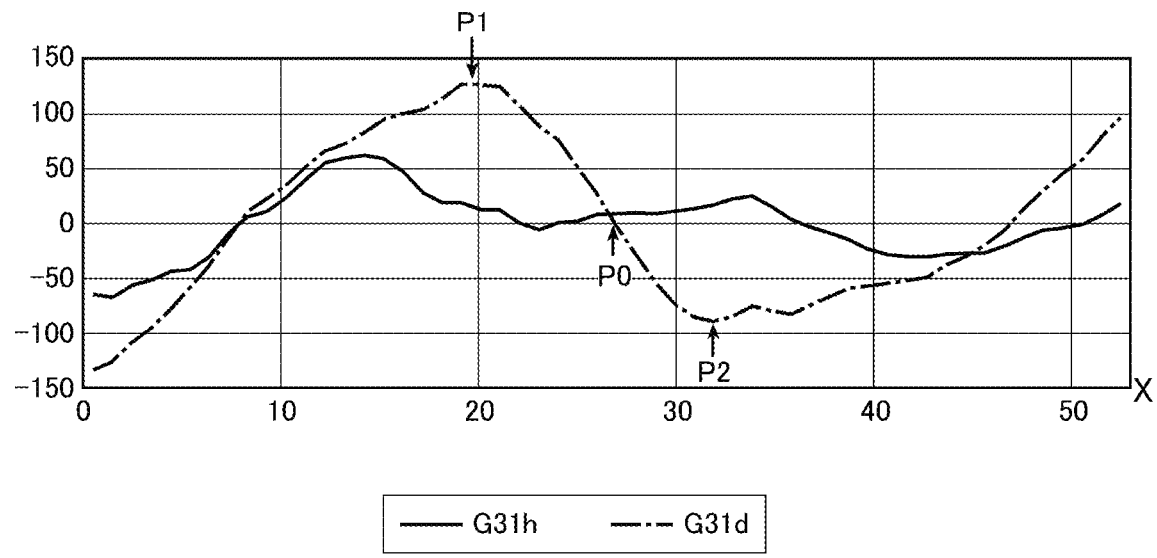
FIG. 18 shows graphs of determination data equivalent to differences between first measurement data and second measurement data shown in FIG. 16A and FIG. 16B.

In the case of adopting the first-order approximate expressions, a calculation of subtracting, from a measured value in the graph G15h, a measured value on the same X coordinate in the graph G25h to obtain a graph G31h shown in FIG. 18 is performed. Similarly, a calculation of subtracting, from a measured value in the graph G15d, a measured value on the same X coordinate in the graph G25d to obtain a graph G31d shown in FIG. 18 is performed.

Figure 19:
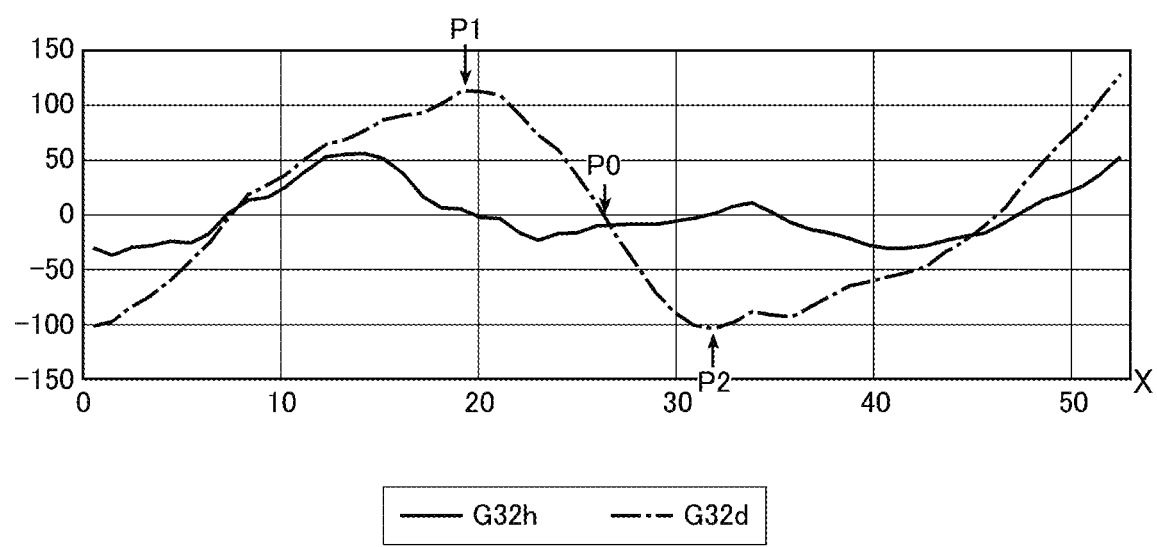
FIG. 19 shows graphs of determination data equivalent to differences between first measurement data and second measurement data shown in FIG. 17A and FIG. 17B.

In the case of adopting the second-order approximate expressions, a calculation of subtracting, from a measured value in the graph G16h, a measured value on the same X coordinate in the graph G26h to obtain a graph G32h shown in FIG. 19 is performed. Similarly, a calculation of subtracting, from a measured value in the graph G16d, a measured value on the same X coordinate in the graph G26d to obtain a graph G32d shown in FIG. 19 is performed.

Next, determination step S31 is executed.

In determination step S31, the presence/absence of an abnormality in the inspection target and, in a case in which an abnormality is present, the location of the abnormality is determined.

First, determination data at the time of an inspection is compared with determination data when the inspection target 8 is sound (the graph G31h or G32h) to determine the presence/absence of an abnormality in the inspection target 8. For example, it is assumed that a graph indicating determination data at the time of the inspection is the graph G31d (or G32d). As shown in FIG. 18 (FIG. 19), the graph G31d (G32d) significantly deviates from the graph G31h (G32h) obtained when the inspection target 8 is sound. This is numerically evaluated to determine that an abnormality is present in the inspection target 8. When looking at the graphs in more detail, a positive peak P1 and a negative peak P2 in the graph G31d (G32d) appear at significant distances from the graph G31h (G32h) obtained when the inspection target 8 is sound. This is numerically evaluated to determine that an abnormality is present in the inspection target 8. A position P0 having a value 0 between the positive peak P1 and the negative peak P2 of the determination data at the time of the inspection is determined as the location of the abnormality in the inspection target 8. This enables the location of the abnormality in the inspection target 8 to be accurately determined.

Determination step S31 may be executed by the cloud computer 9 functioning as a determiner and executing calculations by itself (an automatic determination function). In this case, a determination result (the presence/absence of an abnormality and its location) is displayed to a user via the portable computer 4 or the like.

Alternatively, only determination data (such as a graph) may be displayed to the user via the portable computer 4 or the like, and the user may execute determination step S31 while looking at the determination data.

It goes without saying that both the determination result obtained by the automatic determination function and the determination data may be displayed.

The measurement device 1 may also have a unit that executes the determination data calculation step (S13-16, S23-26, and S30) described above so as to output determination data calculated by the measurement device 1 by itself to the outside. The measurement device 1 may further have the determiner so as to output a determination result to the outside. The output to the outside may be displayed on a display device included in the measurement device 1 itself, or may be output to the cloud computer 9, or may be output to a directly-connected portable computer without passing through the cloud computer 9. This is because the user is able to refer to determination data and a determination result in either case.

(Function Effects and Others)

According to the above-described embodiment of the present invention, in a magnetic non-destructive inspection, a magnetic field component derived from the inspection target 8 is strengthened by the new measurement method of arranging the magnetic field applying unit 3 on one side of the sensor unit 2 and performing measurement, and arranging the magnetic field applying unit 3 on the other side of the sensor unit 2 and performing measurement while following the measurement method of arranging the magnetic field applying unit only on one side of the magnetic sensor, thereby facilitating determination about the presence/absence of a damage in the inspection target 8 and the location of the damage.

As shown in the graphs of FIG. 16A and FIG. 16B or FIG. 17A and FIG. 17B, a magnetic field H2 bulging at the center is a detected magnetic field leaking out of the inspection target 8 between the crossing stirrups 5L and 5R. Magnetic fields H3L and H3R projecting downward on both sides of the magnetic field H2 are changing portions influenced by the crossing stirrups 5L and 5R.

A change caused by the presence of a breakage occurs symmetrically as shown in FIG. 16B or FIG. 17B. This change noticeably appears because the first measurement data measured with the magnetic field applying unit 3 arranged on the one side and the second measurement data measured with the magnetic field applying unit 3 arranged on the other side have been acquired. Consequently, a signal component that varies depending on the state of the inspection target 8 as shown in FIG. 18 or FIG. 19 is noticeably extracted. This facilitates determination about the presence/absence of a damage in the inspection target and the location of the damage.

The magnetic fields H3L and H3R at the changing portions influenced by the crossing stirrups 5L and 5R are offset as shown in FIG. 18 or FIG. 19. This enables a signal component that varies depending on the state of the inspection target 8 to be easily read.

Since a waveform change (H3R) caused by absorption of the magnetic force by crossing reinforcing steel (5) and a waveform change caused by a breakage have similar characteristics as will be understood by referring only to the graph G11d shown in FIG. 12B obtained when the inspection target 8 has a breakage, for example, it is difficult to determine the breakage in accordance with the waveform change. For example, it may be erroneously determined that there is a breakage at the position of H3R looking at the graph G11h shown in FIG. 12A obtained when the inspection target 8 is sound, or it may be erroneously determined that the determined location in the graph G11d shown in FIG. 12B obtained when the inspection target 8 has a breakage is the position of H3R.

In contrast, the above-described embodiment of the present invention facilitates determination about the presence/absence of a damage in the inspection target 8 and the location of the damage as in the example of making determination with reference to the graphs shown in FIG. 18 or FIG. 19.

Determination performance in a non-destructive inspection is improved as described above.

Although the above embodiment has described measurement in the case in which the crossing reinforcing steel (5) is present between the inspection target 8 and the sensor unit 2, the present invention is implemented even in a case in which such crossing reinforcing steel is not provided, and an effect of strengthening a magnetic field component derived from the inspection target is obtained based on the first measurement data and the second measurement data.

The above-described measurement data may be measurement data obtained by the main sensor 21M or may be data constructed by performing correction calculation based on measurement data obtained by the main sensor 21M and measurement data obtained by the reference sensor 21R.

Regardless of the above-described embodiment, an information processing device that performs processing of actualizing a magnetic field component derived from the inspection target is not limited to the cloud computer 9. A hardware configuration is not limited in such a manner that the information processing device may be a computer connected to the measurement device 1 on a one-on-one basis, or a computer integrally mounted on the measurement device 1. In a case in which processing is integrally performed by the cloud computer 9, it is effective in terms of information integration, uniform processing, utilization, and the like.

In the above-described embodiment, the magnetic sensors 21 are of the scanning type in the X direction and of the sensor array type in the Y direction. Alternatively, the sensor unit 2 may be configured such that the magnetic sensors 21 are of the sensor array type also in the X direction, that is, a plurality of the magnetic sensors 21 are arrayed in the first direction X on the enclosure 26, so that a magnetic field distribution in the first direction X in accordance with the distances from the magnetic field applying unit 3 is obtained.

Alternatively, the sensor unit 2 may be configured to be of the scanning type in the X direction and the Y direction.

The above-described embodiment adopts a configuration of acquiring two-dimensional distribution data in a plurality of rows in the X direction and the Y direction but may be implemented as a configuration of acquiring one-dimensional distribution data in one row in the X direction.

Rather than arraying two magnetic sensors 21 in the Z direction, only a single magnetic sensor (main sensor) may be provided in the Z direction.

Although the embodiment of the present invention has been described and illustrated in detail, the scope of the present invention is not limited to the embodiment described above but encompasses the scope of the invention recited in the claims and the equivalent thereof.

What is claimed is:

1. A measurement method of non-destructive inspection in which a magnetic material included in a non-magnetic body is an inspection target, the measurement method comprising:
    measuring that includes:
        application of a magnetic field of a first polarity that is an N polarity or an S polarity from a magnetic field applying unit to the inspection target at an application position through a surface of the non-magnetic body; and
        measurement of a magnetic field from the inspection target with a magnetic sensor on the surface of the non-magnetic body adjacent to the magnetic field applying unit at a plurality of positions having different distances from the magnetic field applying unit in a first direction away from the magnetic field applying unit, the inspection target forming a magnetic field distribution in which magnetic field is attenuated within a range of the first polarity with distance from the magnetic field applying unit,
    wherein
    the measuring includes first measuring and second measuring,
    in the first measuring, measurement is performed with the magnetic field applying unit arranged at an application position on one side in the first direction relative to the plurality of positions at which the magnetic sensor performs measurement, and
    in the second measuring, measurement is performed with the magnetic field applying unit arranged at an application position on a side other than the one side in the first direction relative to the plurality of positions at which the magnetic sensor performs measurement.

2. A measurement device of non-destructive inspection in which a magnetic material included in a non-magnetic body is an inspection target, the measurement device comprising:
    a magnetic field applying unit that applies a magnetic field; and
    a sensor unit that measures a magnetic field, wherein
    the magnetic field applying unit is attachable to and detachable from one end in a first direction of the sensor unit and is attachable to and detachable from another end other than the one end in the first direction of the sensor unit, and
    the sensor unit measures a magnetic field at a plurality of different positions that are at least along a first direction.

3. The measurement device of non-destructive inspection according to claim 2, wherein
    the magnetic field applying unit attachable to and detachable from the one end is attachable to and detachable from the other end.

4. The measurement device of non-destructive inspection according to claim 2, wherein
    the sensor unit has a magnetic sensor that senses magnetic fields in three-axis directions.

5. The measurement device of non-destructive inspection according to claim 2, wherein
    the sensor unit has a plurality of magnetic sensors arrayed two-dimensionally in the first direction and a second direction orthogonal to the first direction.

6. The measurement device of non-destructive inspection according to claim 2, wherein
    the measurement device outputs measurement data obtained by the sensor unit to an outside.

7. The measurement device of non-destructive inspection according to claim 6, wherein
    the measurement device outputs, to the outside, first measurement data measured with the sensor unit in a state in which the magnetic field applying unit is arranged on the one end and not arranged on the other end, and second measurement data measured with the sensor unit in a state in which the magnetic field applying unit is arranged on the other end and not arranged on the one end.

8. The measurement device of non-destructive inspection according to claim 6, further comprising:
    a calculator that calculates determination data based on first measurement data and second measurement data, the first measurement data being measured with the sensor unit in a state in which the magnetic field applying unit is arranged on the one end and not arranged on the other end, and the second measurement data being measured with the sensor unit in a state in which the magnetic field applying unit is arranged on the other end and not arranged on the one end, wherein
    the measurement device outputs the determination data to the outside.

9. A non-destructive inspection method in which a magnetic material included in a non-magnetic body is an inspection target, comprising:
    acquiring of measurement data measured by applying a magnetic field of a first polarity that is an N polarity or an S polarity from a magnetic field applying unit to the inspection target through a surface of the non-magnetic body, and by measuring a magnetic field from the inspection target with a magnetic sensor on the surface of the non-magnetic body adjacent to the magnetic field applying unit at a plurality of positions having different distances from the magnetic field applying unit in a first direction away from the magnetic field applying unit, the inspection target forming a magnetic field distribution in which magnetic field is attenuated within a range of the first polarity with distance from the magnetic field applying unit; and
    calculating of determination data to determine a state of the inspection target based on the measurement data obtained in the acquiring, wherein
    in the acquiring, first measurement data and second measurement data are acquired, the first measurement data being measured with the magnetic field applying unit arranged at an application position on one side in the first direction relative to the plurality of positions at which the magnetic sensor performs measurement, and the second measurement data being measured with the magnetic field applying unit arranged at an application position on a side other than the one side in the first direction relative to the plurality of positions at which the magnetic sensor performs measurement, and in the calculating, the determination data is synthesized based on the first measurement data and the second measurement data.

10. The non-destructive inspection method according to claim 9, wherein in the acquiring, complementary measurement data measured under a condition where the magnetic field applied from the magnetic field applying unit to the inspection target is excluded is acquired, and in the calculating, a first subtraction of the complementary measurement data from the first measurement data and a second subtraction of the complementary measurement data from the second measurement data are performed, and the determination data is synthesized based on data after the first subtraction and the second subtraction.

11. The non-destructive inspection method according to claim 10, wherein the complementary measurement data to be subtracted from the first measurement data is measurement data measured in a state in which the magnetic field applying unit is removed from the application position on the one side after the first measurement data is measured, and the complementary measurement data to be subtracted from the second measurement data is measurement data measured in a state in which the magnetic field applying unit is removed from the application position on the other side after the second measurement data is measured.

12. The non-destructive inspection method according to claim 10, wherein the complementary measurement data to be subtracted from the first measurement data is identical to the complementary measurement data to be subtracted from the second measurement data.

13. The non-destructive inspection method according to claim 9, wherein, in the calculating, the first measurement data is subjected to a first distance correction of decreasing reduction in the magnetic field in accordance with the distances from the magnetic field applying unit on the one side, the second measurement data is subjected to a second distance correction of decreasing reduction in the magnetic field in accordance with the distances from the magnetic field applying unit on the other side, and the determination data is synthesized based on data after the first distance correction and the second distance correction.

14. The non-destructive inspection method according to claim 13, wherein, as the first distance correction and the second distance correction, a calculation of multiplying a measured value at a distance by an N-th power of the distance is performed.

15. The non-destructive inspection method according to claim 9, wherein, in the calculating, a first-order approximate expression or a second-order approximate expression is obtained for the first measurement data, a first subtraction of a value of the approximate expression as obtained from the first measurement data is performed, a first-order approximate expression or a second-order approximate expression is obtained for the second measurement data, a second subtraction of a value of the approximate expression as obtained from the second measurement data is performed, and the determination data is synthesized based on data after the first subtraction and the second subtraction.

16. The non-destructive inspection method according to claim 9, wherein whether an abnormality is present or absent in the inspection target is determined based on the determination data during an inspection, and in a case in which an abnormality is present, a position with a value of 0 between a positive peak and a negative peak of the determination data during the inspection is determined as a location of the abnormality in the inspection target.

17. An information processing device of non-destructive inspection in which a magnetic material included in a non-magnetic body is an inspection target, the information processing device comprises a hardware processor that:

acquires measurement data measured by applying a magnetic field of a first polarity that is an N polarity or an S polarity from a magnetic field applying unit to the inspection target through a surface of the non-magnetic body, and by measuring a magnetic field from the inspection target with a magnetic sensor on the surface of the non-magnetic body adjacent to the magnetic field applying unit at a plurality of positions having different distances from the magnetic field applying unit in a first direction away from the magnetic field applying unit, the inspection target forming a magnetic field distribution in which magnetic field is attenuated within a range of the first polarity with distance from the magnetic field applying unit; and calculates determination data to determine a state of the inspection target based on the measurement data obtained in acquiring the measurement data, wherein in acquiring the measurement data, the hardware processor acquires first measurement data and second measurement data, the first measurement data being measured with the magnetic field applying unit arranged at an application position on one side in the first direction relative to the plurality of positions at which the magnetic sensor performs measurement, and second measurement data being measured with the magnetic field applying unit arranged at an application position on the other side in the first direction relative to the plurality of positions at which the magnetic sensor performs measurement, and in calculating the determination data, the hardware processor synthesizes the determination data based on the first measurement data and the second measurement data.

18. The information processing device of non-destructive inspection according to claim 17, wherein in acquiring the measurement data, the hardware processor acquires complementary measurement data measured under a condition where the magnetic field applied from the magnetic field applying unit to the inspection target is excluded, and in calculating the determination data, the hardware processor performs a first subtraction of the complementary measurement data from the first measurement data and a second subtraction of the complementary measurement data from the second measurement data and synthesizes the determination data based on data after the first subtraction and the second subtraction.

19. The information processing device of non-destructive inspection according to claim 18, wherein
the complementary measurement data to be subtracted from the first measurement data is measurement data measured in a state in which the magnetic field applying unit is removed from the application position on the one side after the first measurement data is measured, and
the complementary measurement data to be subtracted from the second measurement data is measurement data measured in a state in which the magnetic field applying unit is removed from the application position on the other side after the second measurement data is measured.

20. The information processing device of non-destructive inspection according to claim 18, wherein
the complementary measurement data to be subtracted from the first measurement data is identical to the complementary measurement data to be subtracted from the second measurement data.

21. The information processing device of non-destructive inspection according to claim 17, wherein,
in calculating the determination data, the hardware processor:
subjects the first measurement data to a first distance correction of decreasing reduction in the magnetic field in accordance with the distances from the magnetic field applying unit on the one side;
subjects the second measurement data to a second distance correction of decreasing reduction in the magnetic field in accordance with the distances from the magnetic field applying unit on the other side; and
synthesizes the determination data based on data after the first distance correction and the second distance correction.

22. The information processing device of non-destructive inspection according to claim 21, wherein,
in calculating the determination data, the hardware processor performs, as the first distance correction and the second distance correction, a calculation of multiplying a measured value at a distance by an N-th power of the distance.

23. The information processing device of non-destructive inspection according to claim 17, wherein
in calculating the determination data, the hardware processor:
obtains a first-order approximate expression or a second-order approximate expression for the first measurement data;
performs a first subtraction of a value of the approximate expression as obtained from the first measurement data;
obtains a first-order approximate expression or a second-order approximate expression for the second measurement data;
performs a second subtraction of a value of the approximate expression as obtained from the second measurement data; and
synthesizes the determination data based on data after the first subtraction and the second subtraction.

24. The information processing device of non-destructive inspection according to claim 17, wherein the hardware processor further determines whether an abnormality is present or absent in the inspection target based on the determination data during an inspection, and in a case in which an abnormality is present, determines a position with a value of 0 between a positive peak and a negative peak of the determination data during the inspection as a location of the abnormality in the inspection target.

25. A non-transitory recording medium storing a computer readable program that causes a computer to function as an information processing device of non-destructive inspection in which a magnetic material included in a non-magnetic body is an inspection target, wherein
the program causes the computer:
to acquire measurement data measured by applying a magnetic field of a first polarity that is an N polarity or an S polarity from a magnetic field applying unit to the inspection target through a surface of the non-magnetic body and by measuring a magnetic field from the inspection target with a magnetic sensor on the surface of the non-magnetic body adjacent to the magnetic field applying unit at a plurality of positions having different distances from the magnetic field applying unit in a first direction away from the magnetic field applying unit, the inspection target forming a magnetic field distribution in which the magnetic field is attenuated within a range of the first polarity with distance from the magnetic field applying unit;
to calculate determination data to determine a state of the inspection target based on the measurement data obtained in acquiring the measurement data;
in acquiring the measurement data, to acquire first measurement data and second measurement data, the first measurement data being measured with the magnetic field applying unit arranged at an application position on one side in the first direction relative to the plurality of positions at which the magnetic sensor performs measurement, and second measurement data being measured with the magnetic field applying unit arranged at an application position on the other side in the first direction relative to the plurality of positions at which the magnetic sensor performs measurement; and
in calculating the determination data, to synthesize determination data based on the first measurement data and the second measurement data.

26. The computer-readable non-transitory recording medium according to claim 25, wherein,
in acquiring the measurement data, the program causes the computer to acquire complementary measurement data measured under a condition where the magnetic field applied from the magnetic field applying unit to the inspection target is excluded, and
in calculating the determination data, the program causes the computer to perform a first subtraction of the complementary measurement data from the first measurement data and a second subtraction of the complementary measurement data from the second measurement data and synthesizes the determination data based on data after the first subtraction and the second subtraction.

27. The computer-readable non-transitory recording medium according to claim 26, wherein
the complementary measurement data to be subtracted from the first measurement data is measurement data measured in a state in which the magnetic field applying unit is removed from the application position on the one side after the first measurement data is measured, and the complementary measurement data to be subtracted from the second measurement data is measurement data measured in a state in which the magnetic field applying unit is removed from the application position on the other side after the second measurement data is measured.

28. The computer-readable non-transitory recording medium according to claim 26, wherein the complementary measurement data to be subtracted from the first measurement data is identical to the complementary measurement data to be subtracted from the second measurement data.

29. The computer-readable non-transitory recording medium according to claim 25, wherein in calculating the determination data, the program causes the computer:
  to subject the first measurement data to a first distance correction of decreasing reduction in the magnetic field in accordance with the distances from the magnetic field applying unit on the one side;
  to subject the second measurement data to a second distance correction of decreasing reduction in the magnetic field in accordance with the distances from the magnetic field applying unit on the other side, and
  to synthesize the determination data based on data after the first distance correction and the second distance correction.

30. The computer-readable non-transitory recording medium according to claim 29, wherein in calculating the determination data, the program causes the computer to perform, as the first distance correction and the second distance correction, a calculation of multiplying a measured value at a distance by an N-th power of the distance.

31. The computer-readable non-transitory recording medium according to claim 25, wherein in calculating the determination data, the program causes the computer:
  to obtain a first-order approximate expression or a second-order approximate expression for the first measurement data;
  to perform a first subtraction of a value of the approximate expression as obtained from the first measurement data,
  to obtain a first-order approximate expression or a second-order approximate expression for the second measurement data;
  to perform a second subtraction of a value of the approximate expression as obtained from the second measurement data; and
  to synthesize the determination data based on data after the first subtraction and the second subtraction.

32. The computer-readable non-transitory recording medium according to claim 25, wherein the program further causes the computer to determine whether an abnormality is present or absent in the inspection target based on the determination data during an inspection, and in a case in which an abnormality is present, to determine a position with a value of 0 between a positive peak and a negative peak of the determination data during the inspection as a location of the abnormality in the inspection target.

* * * * *